(12) United States Patent
Foley et al.

(10) Patent No.: US 10,220,176 B2
(45) Date of Patent: *Mar. 5, 2019

(54) AEROSOL DELIVERY SYSTEM

(71) Applicant: TRUDELL MEDICAL INTERNATIONAL, London (CA)

(72) Inventors: Martin P. Foley, London (CA); Jerry Grychowski, Lake Zurich, IL (US); Adam Meyer, London (CA); James N. Schmidt, London (CA)

(73) Assignee: TRUDELL MEDICAL INTERNATIONAL, London, Ontario (CA)

( * ) Notice: Subject to any disclaimer, the term of this patent is extended or adjusted under 35 U.S.C. 154(b) by 610 days.

This patent is subject to a terminal disclaimer.

(21) Appl. No.: 14/513,494

(22) Filed: Oct. 14, 2014

(65) Prior Publication Data

US 2016/0136379 A1 May 19, 2016

Related U.S. Application Data

(63) Continuation of application No. 13/414,909, filed on Mar. 8, 2012, now Pat. No. 8,875,706, which is a (Continued)

(51) Int. Cl.
*A61M 16/00* (2006.01)
*A61M 16/14* (2006.01)
(Continued)

(52) U.S. Cl.
CPC .......... *A61M 16/14* (2013.01); *A61M 15/009* (2013.01); *A61M 15/0015* (2014.02);
(Continued)

(58) Field of Classification Search
CPC .......... A61M 15/0086; A61M 16/0084; A61M 15/0018; A61M 15/009; A61M 15/0015;
(Continued)

(56) References Cited

U.S. PATENT DOCUMENTS 3,028,873 A 4/1962 Kindred
3,726,274 A 4/1973 Bird et al.
(Continued)

FOREIGN PATENT DOCUMENTS

CA 2 210 721 A1 7/1996
CA 2 329 126 A1 10/1999
(Continued)

OTHER PUBLICATIONS

Cole, Cynthia, H., MD, "The Use of Aerosolized Medicines in Neonates," Neonatal Respiratory Diseases, vol. 10, No. 4; Associates in Medical Marketing Co., Inc., Newtown, PA.; 2000, 6 pages.
(Continued)

*Primary Examiner* — Steven O Douglas
(74) *Attorney, Agent, or Firm* — Brinks Gilson & Lione

(57) ABSTRACT

Ventilator circuit aerosol delivery systems used to administer medication to a patient are disclosed. In one implementation, a metered dose inhaler ("MDI") ventilator assembly may include a housing that defines an interior space, an inhalation port that defines an inhalation passageway in communication with the interior space, an exhalation port that defines an exhalation passageway in communication with the interior space, a patient port that defines a patient passageway in communication with the interior space, and a MDI receptacle positioned on the housing and in communication with the interior space. The MDI receptacle is operative to receive a MDI container and dispense an aerosolized medication within the MDI container into the interior space so that during inhalation, an inhalation flow including the aerosolized medication may flow through the inhalation port, the interior space, and the patient port. Conversely, during exhalation, gases, moisture, condensation, and/or mucus expelled from the patient flow through the patient port, the interior space, and the exhalation port.

18 Claims, 29 Drawing Sheets

Related U.S. Application Data continuation of application No. 12/105,881, filed on Apr. 18, 2008, now Pat. No. 8,151,794.

(60) Provisional application No. 60/926,108, filed on Apr. 24, 2007.

(51) Int. Cl.
| | | |
|---|---|---|
| *A61M 15/00* | (2006.01) | |
| *A61M 16/04* | (2006.01) | |
| *A61M 16/08* | (2006.01) | |
| *A61M 16/20* | (2006.01) | |

(52) U.S. Cl.
CPC .... *A61M 15/0018* (2014.02); *A61M 15/0068* (2014.02); *A61M 15/0086* (2013.01); *A61M 16/0003* (2014.02); *A61M 16/0009* (2014.02); *A61M 16/0084* (2014.02); *A61M 16/04* (2013.01); *A61M 16/0816* (2013.01); *A61M 16/0833* (2014.02); *A61M 16/0841* (2014.02); *A61M 16/0858* (2014.02); *A61M 16/208* (2013.01); *A61M 16/0078* (2013.01); *A61M 16/08* (2013.01); *A61M 16/085* (2014.02); *A61M 2016/0027* (2013.01); *A61M 2205/0233* (2013.01); *A61M 2205/3331* (2013.01); *A61M 2205/3368* (2013.01)

(58) Field of Classification Search
CPC .......... A61M 16/08; A61M 2205/0233; A61M 16/0078; A61M 16/14; A61M 15/0068; A61M 16/003; A61M 16/04; A61M 16/0816; A61M 16/208; A61M 16/0009; A61M 16/0833; A61M 16/0841; A61M 16/0858; A61M 2016/0027; A61M 2205/3331; A61M 2205/3368; A61M 16/085

See application file for complete search history.

(56) References Cited

U.S. PATENT DOCUMENTS

| | | | |
|---|---|---|---|
| 4,333,451 | A | 6/1982 | Paluch |
| 4,534,343 | A | 8/1985 | Nowacki et al. |
| 4,803,977 | A | 2/1989 | Kremer et al. |
| 4,938,210 | A | 7/1990 | Shene |
| 4,984,158 | A | 1/1991 | Hillsman |
| 5,002,048 | A | 3/1991 | Makiej, Jr. |
| 5,005,572 | A | 4/1991 | Raemer et al. |
| 5,012,804 | A | 5/1991 | Foley et al. |
| 5,020,530 | A | 6/1991 | Miller |
| 5,178,138 | A | 1/1993 | Walstrom |
| 5,357,946 | A | 10/1994 | Kee et al. |
| 5,617,844 | A | 4/1997 | King |
| 5,647,345 | A | 7/1997 | Saul |
| 5,666,946 | A | 9/1997 | Langenback |
| 5,693,944 | A | 12/1997 | Rich |
| 5,738,087 | A | 4/1998 | King |
| 5,816,240 | A | 10/1998 | Komesaroff |
| 5,848,587 | A | 12/1998 | King |
| 6,014,972 | A | 1/2000 | Sladek |
| 6,039,042 | A | 3/2000 | Sladek |
| 6,269,810 | B1 | 8/2001 | Brooker et al. |
| 6,279,574 | B1 | 8/2001 | Richardson et al. |
| 6,390,091 | B1 | 5/2002 | Banner et al. |
| 6,435,177 | B1 | 8/2002 | Schmidt et al. |
| 6,527,011 | B1 | 3/2003 | Mantz |
| 6,581,600 | B2 | 6/2003 | Bird |
| 6,805,118 | B2 | 10/2004 | Brooker et al. |
| 6,886,561 | B2 | 5/2005 | Bayron et al. |
| 7,201,164 | B2 | 4/2007 | Grychowski et al. |
| 7,201,167 | B2 | 4/2007 | Fink et al. |
| 7,445,006 | B2 | 11/2008 | Dhuper et al. |
| 2002/0069870 | A1 | 6/2002 | Farmer |
| 2002/0104531 | A1 | 8/2002 | Malone |
| 2003/0131844 | A1 | 7/2003 | Kumar et al. |
| 2004/0003808 | A1 | 1/2004 | Fuhrman et al. |
| 2005/0005929 | A1 | 1/2005 | Snyder et al. |
| 2005/0039746 | A1 | 2/2005 | Grychowski et al. |
| 2005/0217666 | A1 | 10/2005 | Fink et al. |
| 2005/0217667 | A1 | 10/2005 | Dhuper et al. |
| 2005/0247312 | A1 | 11/2005 | Davies |
| 2005/0274378 | A1 | 12/2005 | Bonney et al. |
| 2006/0078506 | A1 | 4/2006 | Niven et al. |
| 2006/0254579 | A1 | 11/2006 | Grychowski et al. |
| 2008/0015475 | A1 | 1/2008 | Lau et al. |

FOREIGN PATENT DOCUMENTS

| | | |
|---|---|---|
| CA | 2 354 561 A1 | 6/2000 |
| CA | 2 493 078 A1 | 2/2004 |
| CA | 2 515 593 A1 | 8/2004 |
| CA | 2 424 731 A1 | 10/2004 |
| EP | 0 281 650 A1 | 9/1988 |
| EP | 0 972 534 A2 | 1/2000 |
| EP | 0 972 534 A3 | 1/2000 |
| GB | 750 152 A | 6/1953 |
| WO | WO 2004/011071 A1 | 2/2004 |
| WO | WO 2004/071549 A2 | 8/2004 |
| WO | WO 2006/026237 A1 | 3/2006 |
| WO | WO 2006/114699 A2 | 11/2006 |
| WO | WO 2007/030162 A2 | 3/2007 |

OTHER PUBLICATIONS

Shah, Dr. Vibhuti, "A Dose-ranging study to assess the effect of inhaled corticosteroids in ventilated preterm neonates," Sunnybrook and Women's College Health Sciences Center, date unknown, 27 pages.

International Search Report for International Application No. PCT/IB2004/000333, dated Aug. 30, 2004, 8 pages.

Written Opinion of the International Searching Authority for International Application No. PCT/IB2004/000333, dated Aug. 30, 2004, 9 pages.

International Search Report for International Application No. PCT/IB2006/001027, dated Sep. 21, 2006, 6 pages.

Written Opinion of the International Searching Authority for International Application No. PCT/IB2006/001027, dated Sep. 21, 2006, 8 pages.

Communication Relating to Results of Partial International Search in International Application No. PCT/US2008/061203, dated Aug. 12, 2008, 2 pages.

International Search Report for International Application No. PCT/US2008/061203, dated Nov. 11, 2008, 8 pages.

Written Opinion of the International Searching Authority for International Application No. PCT/US2008/061203, dated Nov. 11, 2008, 9 pages.

International Preliminary Report on Patentability for International Application No. PCT/US2008/061203, dated Nov. 5, 2009, 14 pages.

Reply to Oct. 6, 2008 Office Action in U.S. Appl. No. 10/774,751, dated Jan. 5, 2009, 14 pages.

Office Action from U.S. Appl. No. 10/744,751, dated Jun. 24, 2009, 8 pages.

Office Action from U.S. Appl. No. 11/410,270, dated Jan. 20, 2010, 14 pages.

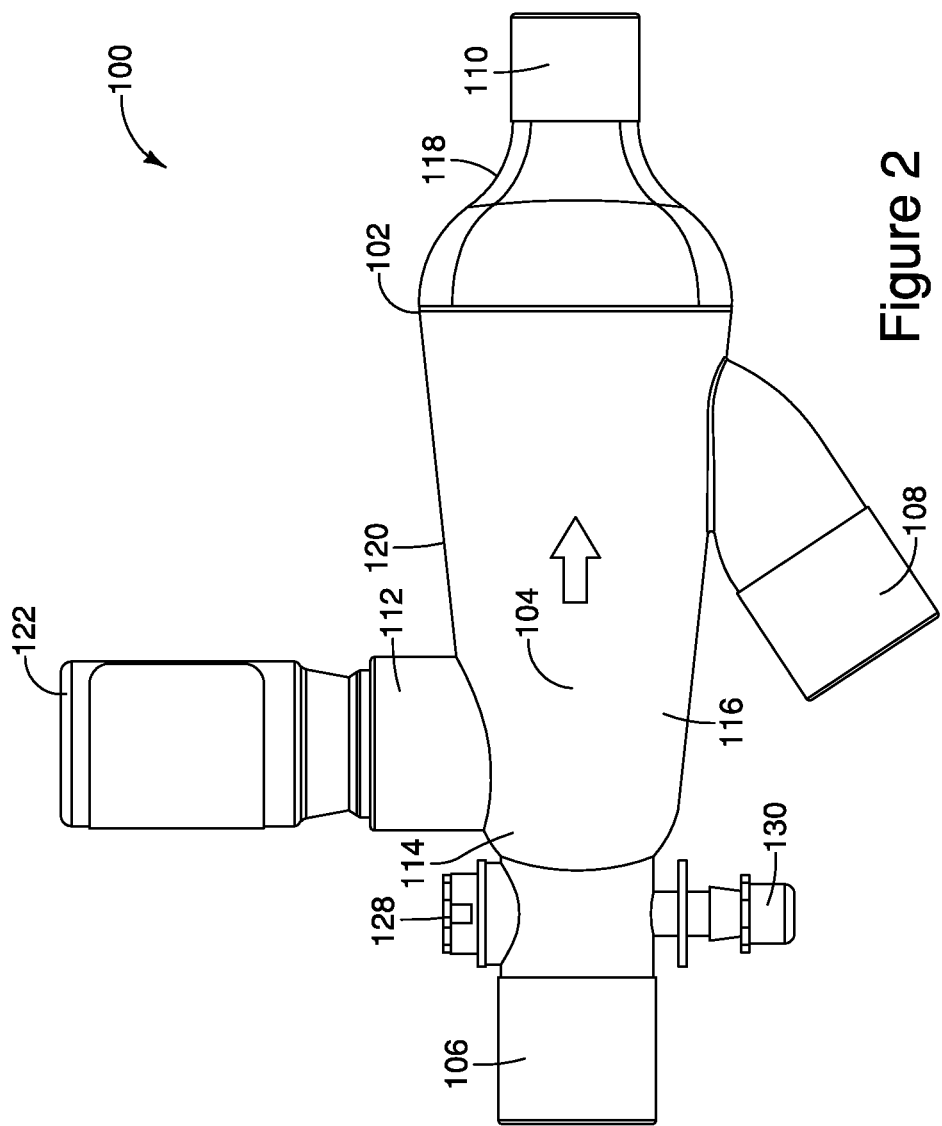

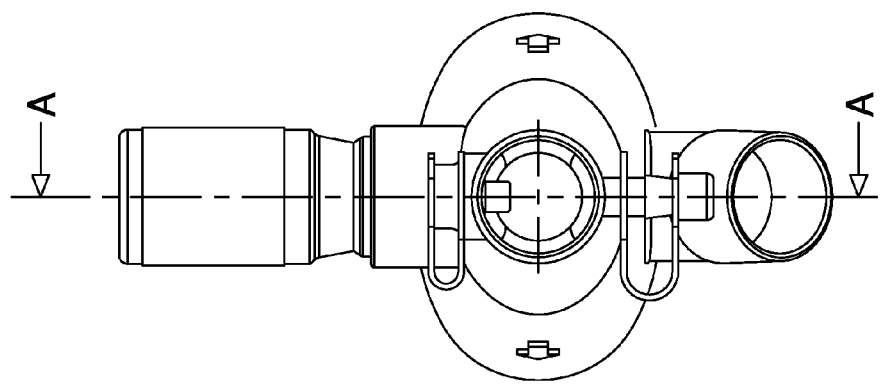
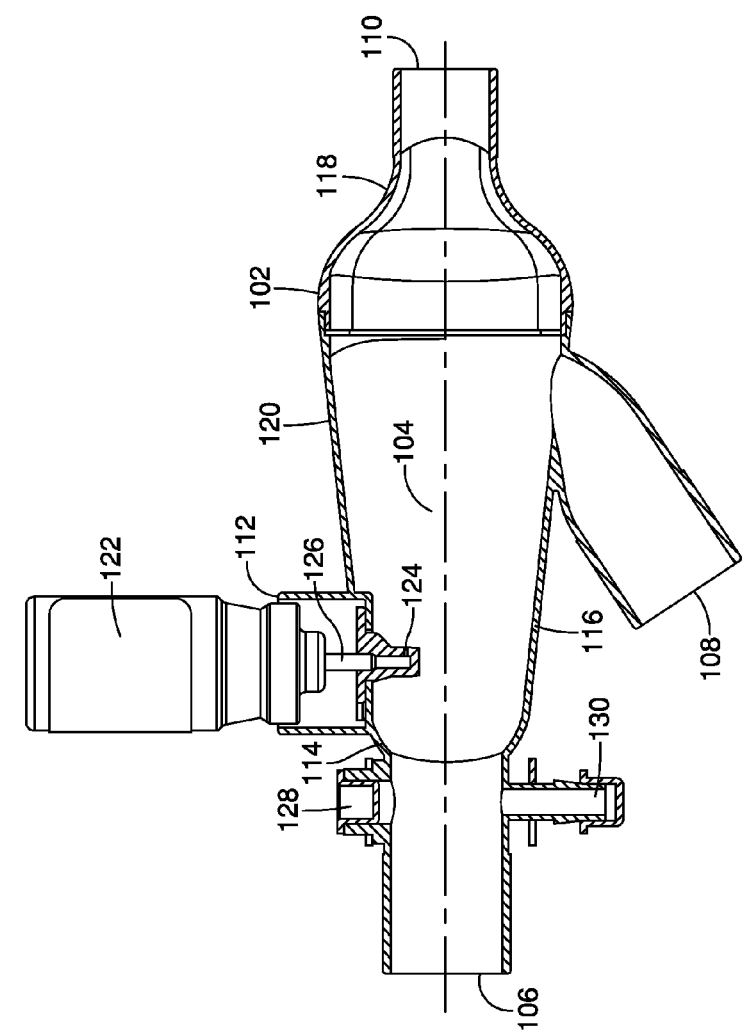

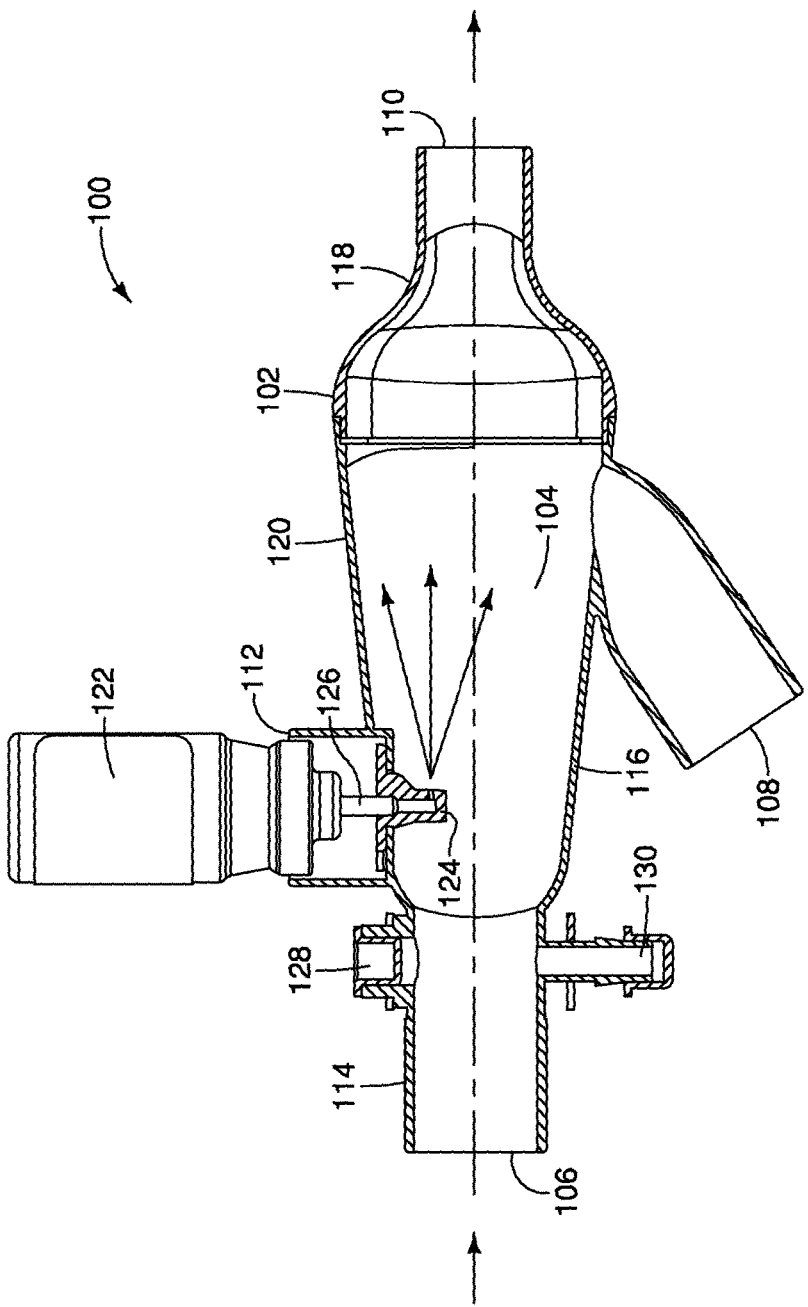

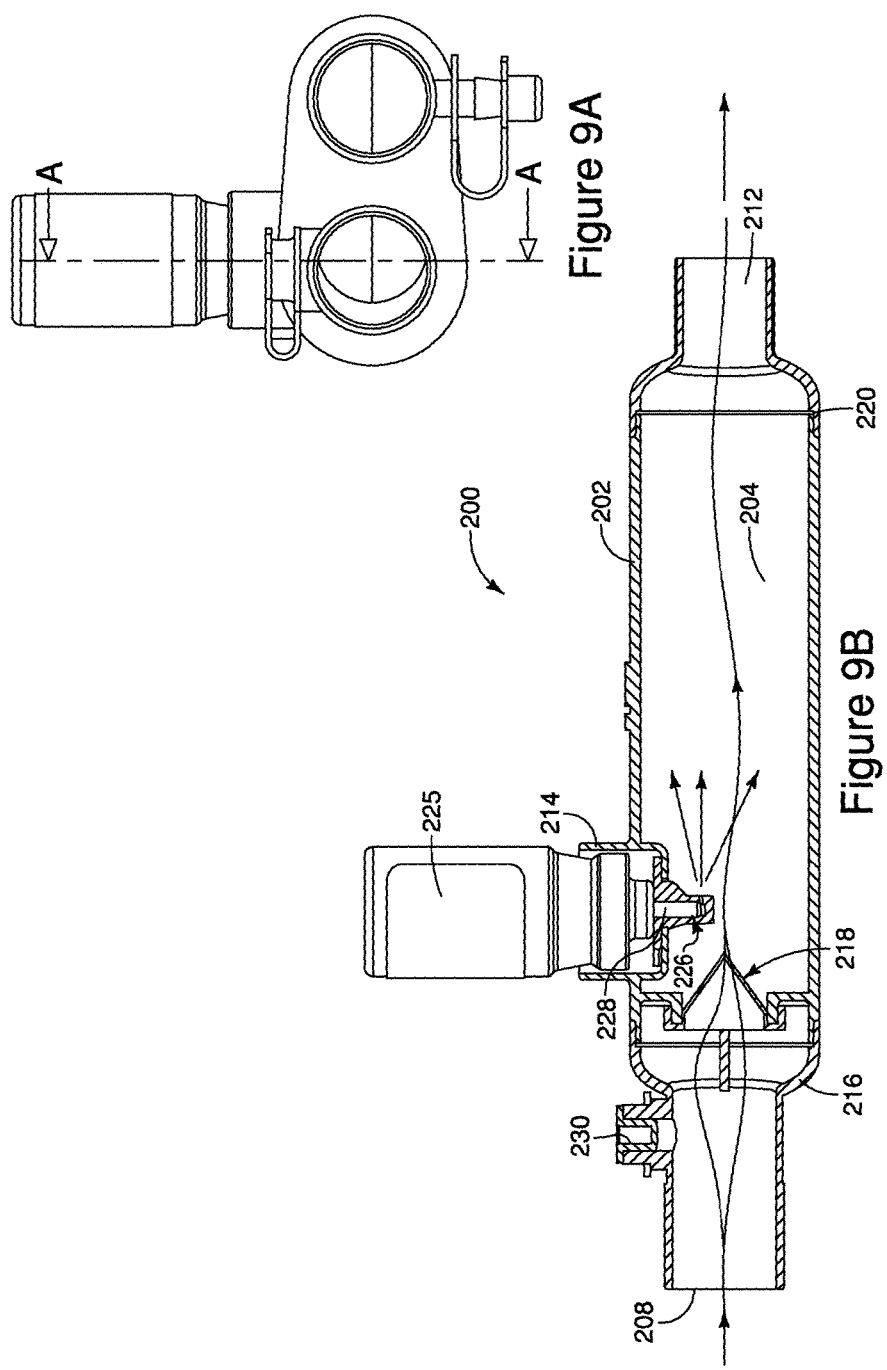

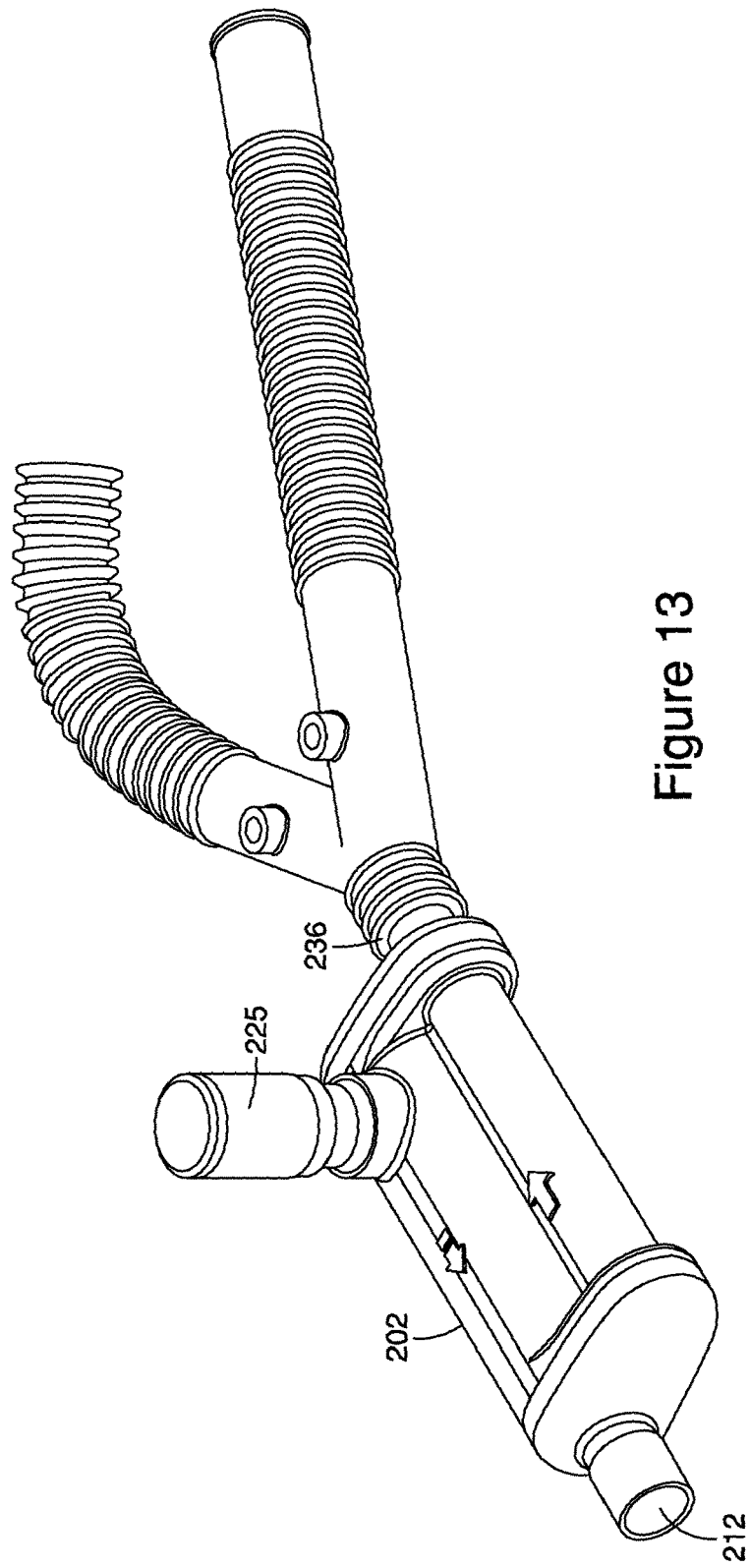

AEROSOL DELIVERY SYSTEM

This application is a continuation of U.S. application Ser. No. 13/414,909, filed Mar. 8, 2012, which application is a continuation of U.S. application Ser. No. 12/105,881, filed Apr. 18, 2008, now U.S. Pat. No. 8,151,794, which application claims the benefit of U.S. Provisional Application No. 60/926,108, filed Apr. 24, 2007, entitled "Ventilator Circuit Aerosol Delivery System," the entire disclosures of which are hereby incorporated herein by reference.

BACKGROUND

Patients with respiratory insufficiency often require continuous mechanical ventilation with a positive-pressure ventilator. In such patients, an endotracheal breathing tube, or a tracheotomy tube, is positioned in the patient's main airway. An internal end of the endotracheal breathing tube is positioned for exchange of air within the lungs and an externally protruding end of the endotracheal breathing tube is connected with a ventilator circuit of a ventilator system. The ventilator system provides heated, humidified, filtered breathable air at a prescribed respirable rate, tidal volume or pressure, and FiO2 to a patient in repetitive respiration cycles.

It is frequently necessary to use a Metered Dose Inhaler ("MDI") to deliver a prescribed amount of an aerosolized drug into an air stream that is forced through an inspiratory phrase of a ventilator system. In the present practice, to engage a MDI ventilator assembly with a ventilator circuit, an inspiratory hose is disconnected from a ventilator at a Wye connector, and the MDI ventilator assembly is used to reconnect the inspiratory hose to the Wye connector. The aerosolized drug is dispensed into an inspiratory stream, and upon completion of the therapy, the MDI ventilator assembly is removed from the inspiratory side of the ventilator circuit.

There are a number of problems with this practice. For example, due to the distance from an inspired limb of a ventilation circuit to an end of an endotracheal tube leading to a patient, loss of the aerosolized drug dispensed in the inspired limb often occurs before reaching the patient.

Another problem with present MDI ventilator assemblies is that they may not be attached directly to an endotracheal tube and left in connection to a main ventilator circuit because it presents a "dead space area" where gases exhaled from a patient remain between each breath such that the same gases are inhaled by the patient upon their next breath. For example, neonates often require aerosol medication, which can be difficult to administer due to the small airway size and because ventilation is required immediately after birth.

In addition, it is desirable to provide for aerosol medication delivery in conjunction with a resuscitation bag, which may be connected to an oxygen supply. Importantly, such systems must maintain a positive-end expiratory pressure (PEEP) for patients that have been intubated.

For at least these reasons, improved MDI ventilator assemblies are desirable.

BRIEF DESCRIPTION OF THE DRAWINGS

FIG. 2 is a side view of the MDI ventilator assembly of FIG. 1;

FIG. 3a is a front view of the MDI ventilator assembly of FIG. 1;

FIG. 3b is an illustration of a cross-section of the MDI ventilator assembly cut at line A of FIG. 3a;

FIG. 4 is a side view of the MDI ventilator assembly of FIG. 1 illustrating an inhalation path from an inhalation limb of a ventilator to a patient;

FIG. 9a is a front view of the MDI ventilator assembly of FIG. 7;

FIG. 9b is an illustration of a cross-section of the MDI ventilator assembly cut at line A of FIG. 9a;

FIG. 10b is an illustration of a cross-section of the MDI ventilator assembly cut at line A of FIG. 10a;

FIG. 11a is a side view of the MDI ventilator assembly of FIG. 7;

FIG. 11b is an illustration of a cross-section of the MDI ventilator assembly cut at line A of FIG. 11a;

FIG. 13 is a perspective view of the MDI ventilator assembly of FIG. 12;

FIG. 14b is an illustration of a cross-section of the MDI ventilator assembly cut at line A of FIG. 14a;

FIG. 15b is an illustration of a cross-section of the MDI ventilator assembly cut at line A of FIG. 15a.

DETAILED DESCRIPTION OF THE DRAWINGS

Figure 1:
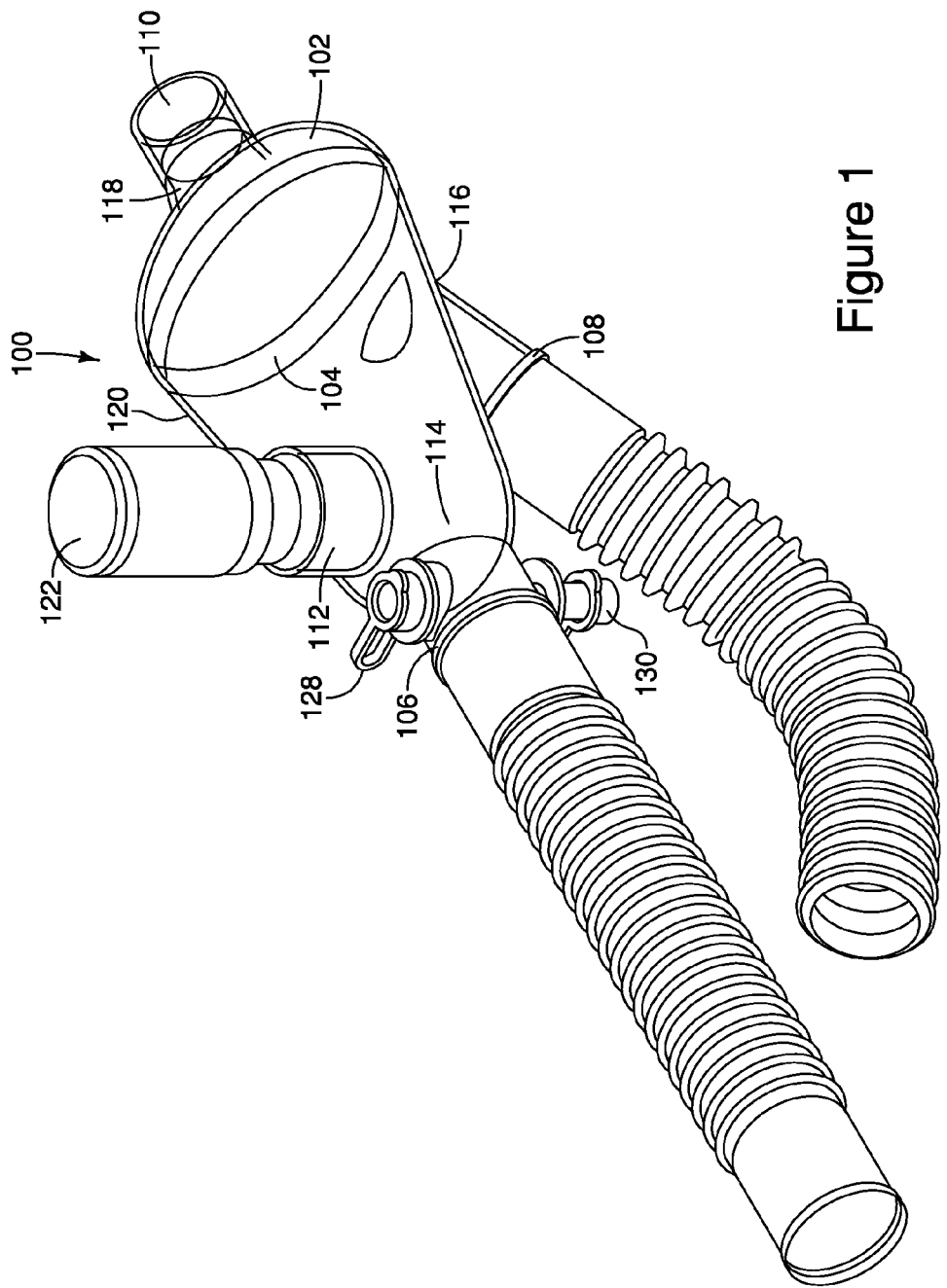
FIG. 1 is a perspective view of one embodiment of a MDI ventilator assembly.

The present disclosure is directed to ventilator circuit aerosol delivery systems. The disclosed ventilator circuit aerosol delivery systems include implementations to be used with intermittent flow ventilators and implementations to be used with continuous flow ventilators. As described in more detail below, by implementing systems to separate an inspired gas flow from an expired gas flow at the entrance to an endotracheal tube, or a tracheotomy tube, and integrating a Wye connector into an MDI ventilator assembly, the MDI ventilator assembly may be moved from the inspired limb and connected directly to the endotracheal tube, or a tracheotomy tube. By connecting the MDI ventilator assembly directly to the endotracheal tube, or tracheotomy tube, aerosolized drugs may be more effectively administered to a patient without "dead space area" where gases exhaled from a patient remain between each breath such that the same gases are inhaled by the patient upon their next breath FIGS. 1-6 illustrate embodiments of a MDI ventilator assembly 100 used in intermittent flow ventilator systems. The MDI ventilator assembly 100 includes a housing 102 that defines an interior space 104. In one implementation, the interior space 104 may taper out as shown in FIGS. 1-6 to allow an aerosolized drug to expand within the interior space 104 before being inhaled by a patient.

Preferably, the housing 102 is made of a clear plastic, although it can be non-transparent in certain embodiments. In one implementation, the housing 102 may be made from an antistatic material such that a surface resistivity of the housing 102 is less than about 10E12 ohm/sq., and preferably between about 10E10 and about 10E12 ohm/sq. Examples of antistatic housings are disclosed in U.S. patent application Ser. No. 10/821,260, filed Apr. 8, 2004, the entirety of which is hereby incorporated by reference. Further examples of housings used in MDI ventilator assemblies are disclosed in U.S. patent application Ser. No. 10/774,751, filed Feb. 9, 2004, and U.S. patent application Ser. No. 11/410,270, filed Apr. 24, 2006, the entirety of each of which is hereby incorporated by reference.

The housing 102 additionally defines an inhalation port 106, an exhalation port 108, a patient port 110, and a MDI receptacle 112. It should be understood that the term port is meant to include connectors that insert into a limb or tube of a ventilation system (a male connector) as well as connectors that receive a limb or tube of a ventilation system (a female connector).

The inhalation port 106 is typically located on a first distal end 114 of the housing 102, but the inhalation port 106 may be located at other positions on the housing 102. The inhalation port 106 defines an inhalation passageway into the interior space 104 of the housing 102. In one implementation, the inhalation port 106 may be annular in shape with a radius such as 22 mm so that the inhalation port 106 may be inserted into, and coupled with, an inhalation limb of a ventilator system to form an airtight seal. However, the inhalation port 106 may be other shapes and sizes such. For example, the inhalation port 106 may be shapes such as a triangular port or a square port.

The exhalation port 108 is typically located on a bottom 116 of the housing 102, but the exhalation port 108 may be located at other positions on the housing 102. The exhalation port 108 defines an exhalation passageway from the interior space 104 of the housing 102. In one implementation, the exhalation port 108 may be shaped in an annular manner with a radius such as 22 mm so that the exhalation port 108 may be inserted into, and coupled with, an exhalation limb of a ventilator system to form an aright seal. However, the exhalation port 108 may be other sizes and shapes. For example, the exhalation port 108 may be shapes such as a triangular port or a square port.

The patient port 110 is typically located on a second distal end 118 of the housing 102 that opposes the first distal end 114 of the housing 102 that includes the inhalation port 106, but the patient port 110 may be located at other positions on the housing 102. The patient port 110 may be shaped in an annular manner with a radius such as 15 mm so that the patient port 110 may be inserted into, and coupled with, an endotracheal breathing tube, or a tracheotomy tube, of a patient to form an airtight seal. However, the patient port 110 may be other sizes and shapes. For example, the patient port 110 may be shapes such as a triangular port or a square port.

The MDI receptacle 112 is typically located on a top 120 of the housing 102, but the MDI receptacle 112 may be located at other positions on the housing 102. The MDI receptacle 112 is positioned away from the patient port 110 such that, as explained in more detail below, when an aerosolized drug is dispensed into the interior space 104 via the MDI receptacle 112, the aerosolized drug may expand before being inhaled by a patient via the patient port 110.

The MDI receptacle 112 may define a socket or recess to receive an end of a MDI container 122 such that when the MDI container 122 is placed in the MDI receptacle 112, an actuator nozzle 124 in the recess of the MDI receptacle 112 engages a stem 126 extending from the MDI container 122 and causes the aerosolized drug within the MDI container 122 to be dispensed into the interior space 104 of the housing 102. It should be understood that the receptacle can be configured to connect to and support medication containers, aerosol dispersal devices, or systems other than the disclosed MDI containers 122.

During operation, gases for inhalation and exhalation flow through the MDI ventilator assembly 100. Referring to FIG. 4, during inhalation, gases flow from the inhalation limb into the interior space 104 via the inhalation port 106, and flow from the interior space 104 to the endotracheal breathing tube, or tracheotomy tube, via the patient port 110. As described above, when a MDI container 122 is inserted into the MDI receptacle 112, the actuator nozzle 118 of the MDI receptacle 112 engages a stem 126 extending from the MDI container 122 and causes an aerosolized drug to be dispensed into the interior space 104. Therefore, it will be appreciated that during inhalation, when gases flow from the interior space 104 to the endotracheal breathing tube, or tracheotomy tube, the aerosolized drug expands and flows to the patient. Further, if any portion of the aerosolized drug is not inhaled during an initial breath, the remaining aerosolized drug is inhaled during subsequent breaths.

Figure 5:
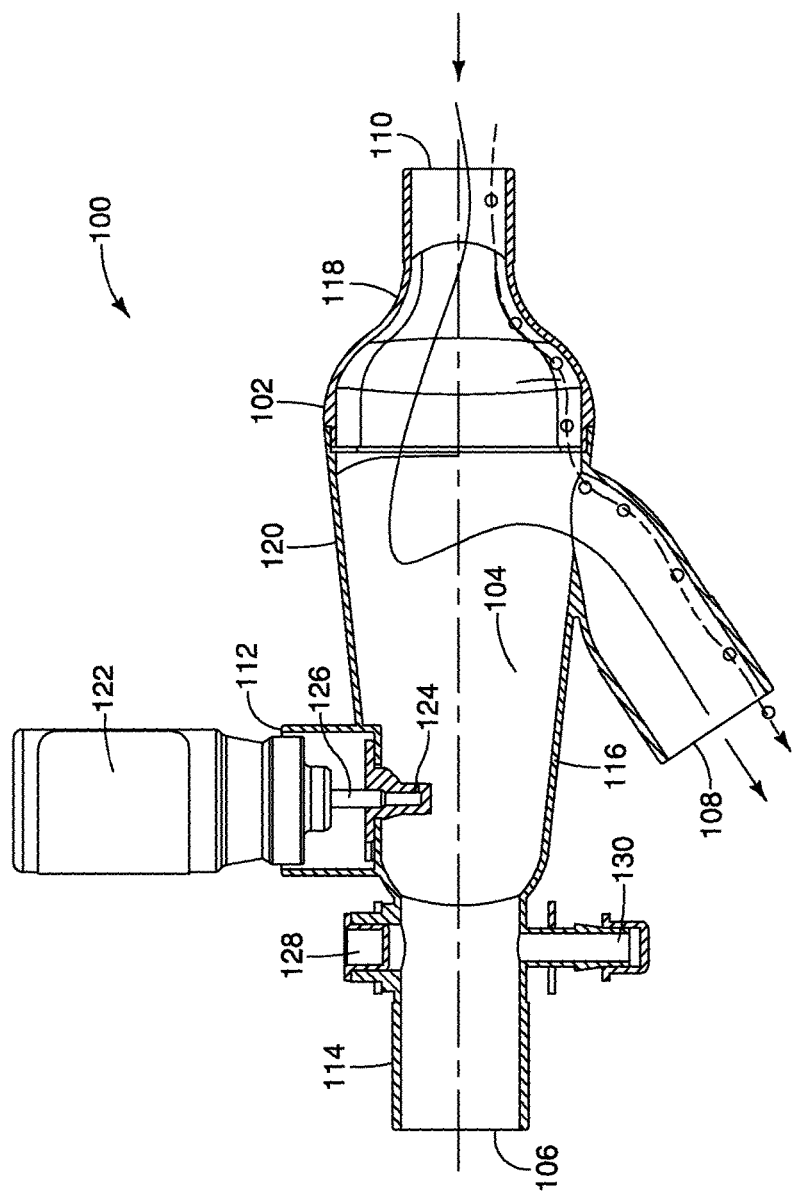
FIG. 5 is a side view of the MDI ventilator assembly of FIG. 1 illustration an exhalation path from a patent to an exhalation limb of a ventilator.

Referring to FIG. 5, during exhalation, gases, moisture, condensation, and/or mucus flow from the endotracheal breathing tube, or tracheotomy tube, to the interior space 104 via the patient port 110, and flow from the interior space 104 to the exhalation limb via the exhalation port 108, the axis of which forms an acute angle (between 0 and 90 degrees) relative to the axis of the patient port 110 or the axis of the inhalation port 106. In one implementation, the interior space and exhalation port are angled down from the patient port 110 to the exhalation port 108 to assist in removing moisture, condensation, and/or mucus from the interior space 104.

Because most of the gases, moisture, condensation, and/or mucus expelled by a patient flow out of the interior space 104 to the exhalation limb during exhalation, during subsequent inhalation, the amount of gases, moisture, condensation, and/or mucus that are rebreathed by the patient is reduced.

Figure 6:
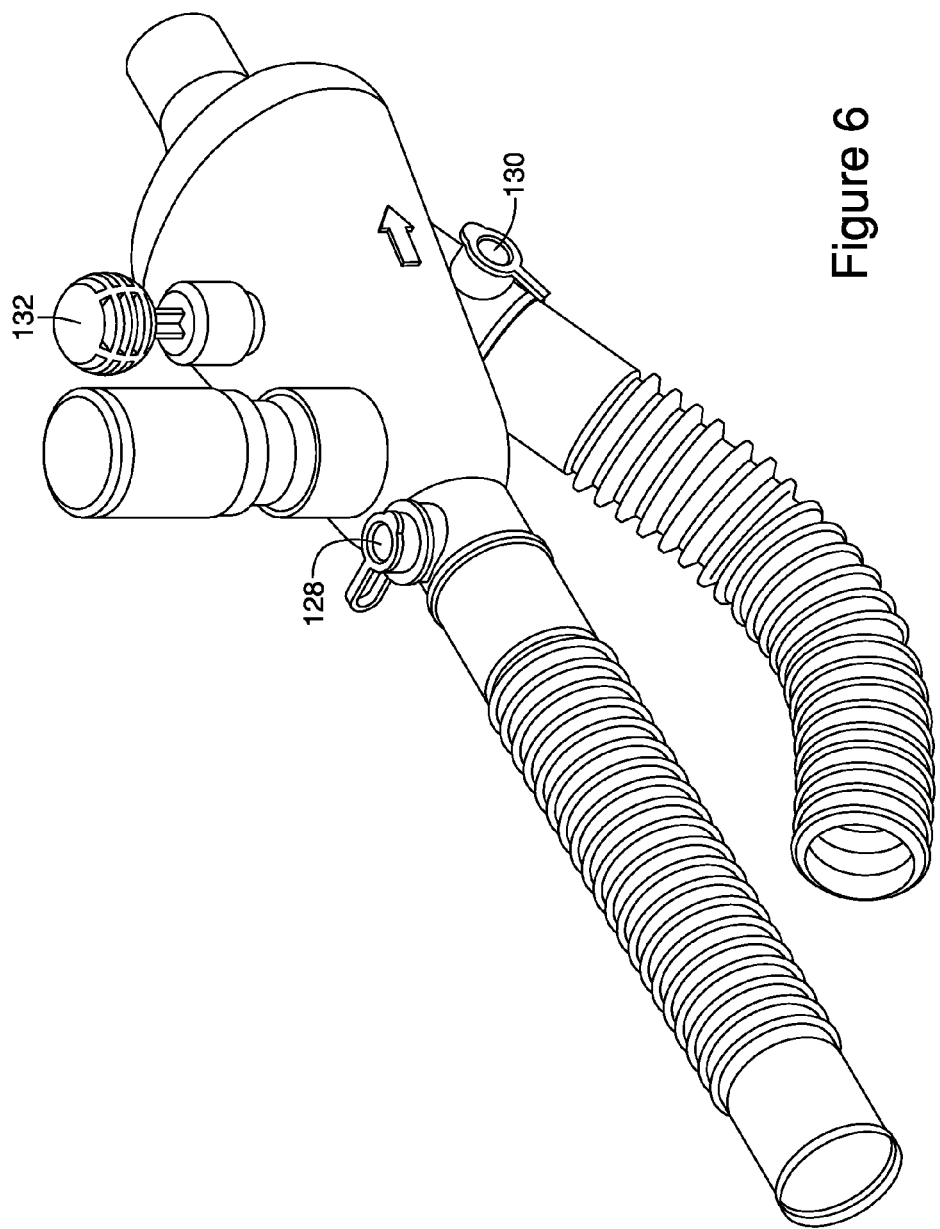
FIG. 6 is a perspective view of another embodiment of a MDI ventilator assembly.

As seen in FIGS. 1 and 6, the housing may additionally define a temperature probe port 128, a pressure port 130, and a holder 132. In one implementation, both the temperature probe port 128 and the pressure port 130 are positioned on the inhalation port 106. However, in other implementations, one or both of the temperature probe port 128 and the pressure port 130 may be positioned on other portions of the housing such as the exhalation port 108. It should be understood that the ports, including without limitation the temperature and pressure ports, can be used to monitor other parameters, such as the presence of $CO_2$ or other gases.

FIGS. 7-15 illustrate embodiments of a MDI ventilator assembly 100 used in continuous flow ventilator systems. The DMI ventilator assembly 200 includes a housing 202 that defines an inhalation interior space 204 and an exhalation interior space 206. The inhalation interior space 204 and exhalation interior space 206 may be cylindrical in shape, with at least a portion of the exhalation interior space 206 running parallel to the inhalation interior space 204. However, the inhalation interior space 204 and exhalation interior space 206 may be other shapes.

Referring to FIGS. 7-11 and 26, the housing 202 additionally defines an inhalation port 208, an exhalation port 210, a patient port 212, and a MDI receptacle 214. The inhalation port 208 is typically located on a first distal end 216 of the housing 202, but the inhalation port 208 may be located at other positions on the housing 202. The inhalation port 208 defines an inhalation passageway into the inhalation interior space 204. In the embodiment of FIGS. 7-11, a one-way inhalation valve 218 is positioned in the inhalation passageway adjacent the inhalation port to permit one-way flow from the inhalation port 208 to the inhalation interior space 204. The one-way inhalation valve 218 may be a center post valve, a flap valve, a duckbill valve, an annular valve, or any other type of one-way valve known in the art. In the alternative embodiment of FIG. 26, the inhalation valve 218 is located adjacent the patient port at the second end of the housing.

Referring to FIGS. 1-11 and 26, the inhalation port 208 may be shaped in an annular manner with a radius such as 22 mm so that the inhalation port 208 may be inserted into, and coupled with, an inhalation limb of a ventilator system to form an airtight seal. However, the inhalation port 208 may be other sizes and shapes. For example, the inhalation port 208 may be shapes such as a triangular port or a square port.

The exhalation port 210 is typically also located on the first distal end 216 of the housing 202, but the exhalation port 210 may be located at other positions on the housing 202. The exhalation port 210 defines an exhalation passageway into the exhalation interior space 206. The exhalation port 210 may be shaped in an annular manner with a radius such as 22 mm so that the exhalation port 210 may be inserted into, and coupled with, an exhalation limb of the ventilator system to form an airtight seal. However, the exhalation port 210 may be other sizes and shapes. For example, the exhalation port 210 may be shapes such as a triangular port or a square port.

The patient port 212 is typically located on a second distal end 220 of the housing 202 that opposes the first distal end 216 including the inhalation port 208 and the exhalation port 210. However, the patient port 212 may be located at other positions on the housing 202. The patient port 212 defines a patient passageway that is in communication with both the inhalation interior space 204 and the exhalation interior space 206. In some implementations, the patient port 212 may be positioned on the second distal end 220 of the housing 202 so that the patient port 212 substantially aligns with the inhalation port 208 to assist in the inhalation of gases and aerosolized drugs from the inhalation interior space 204, as explained in more detail below.

A one-way exhalation valve 222 is positioned at an end 224 of the exhalation interior space 206, adjacent the patient port 212, to permit one-way flow from the patient port 212 to the exhalation interior space 206 while not affecting the flow of gases from the inhalation interior space 204 to the patient port 212. The one-way exhalation valve 222 may be a center post valve, a flap valve, a duckbill valve, an annular valve, or any other type of one-way valve known in the art.

The patient port 212 may be shaped in an annular manner with a radius such as 15 mm so that the patient port 110 may be inserted into, and coupled with, an endotracheal breathing tube, or a tracheotomy tube, of a patient to form an airtight seal. However, the patient port 212 may be other sizes and shapes. For example, the patient port 212 may be shapes such as a triangular port or a square port.

The MDI receptacle 214 is typically located on a top 222 of the housing 202, but the MDI receptacle 214 may be located at other positions on the housing 202. The MDI receptacle 214 is positioned away from the patient port 212 such that, as explained in more detail below, when an aerosolized drug is dispensed into the inhalation interior space 204 via the MDI receptacle 214, the aerosolized drug may expand before being inhaled by a patient via the patient port 212.

The MDI receptacle may define a socket or recess to receive an end of a MDI container 225 such that when the MDI container 225 is placed in the MDI receptacle 214, an actuator nozzle 226 in the recess of the MDI receptacle 214 engages a stem 228 extending from the MDI container 225 and causes the aerosolized drug within the MDI container 224 to be dispensed into the inhalation interior space 204 of the housing 202. It should be understood that the receptacle can be configured to connect to and support medication containers, aerosolized dispersion devices, or systems other than the disclosed MDI containers 225.

Figures 11A, 11B:
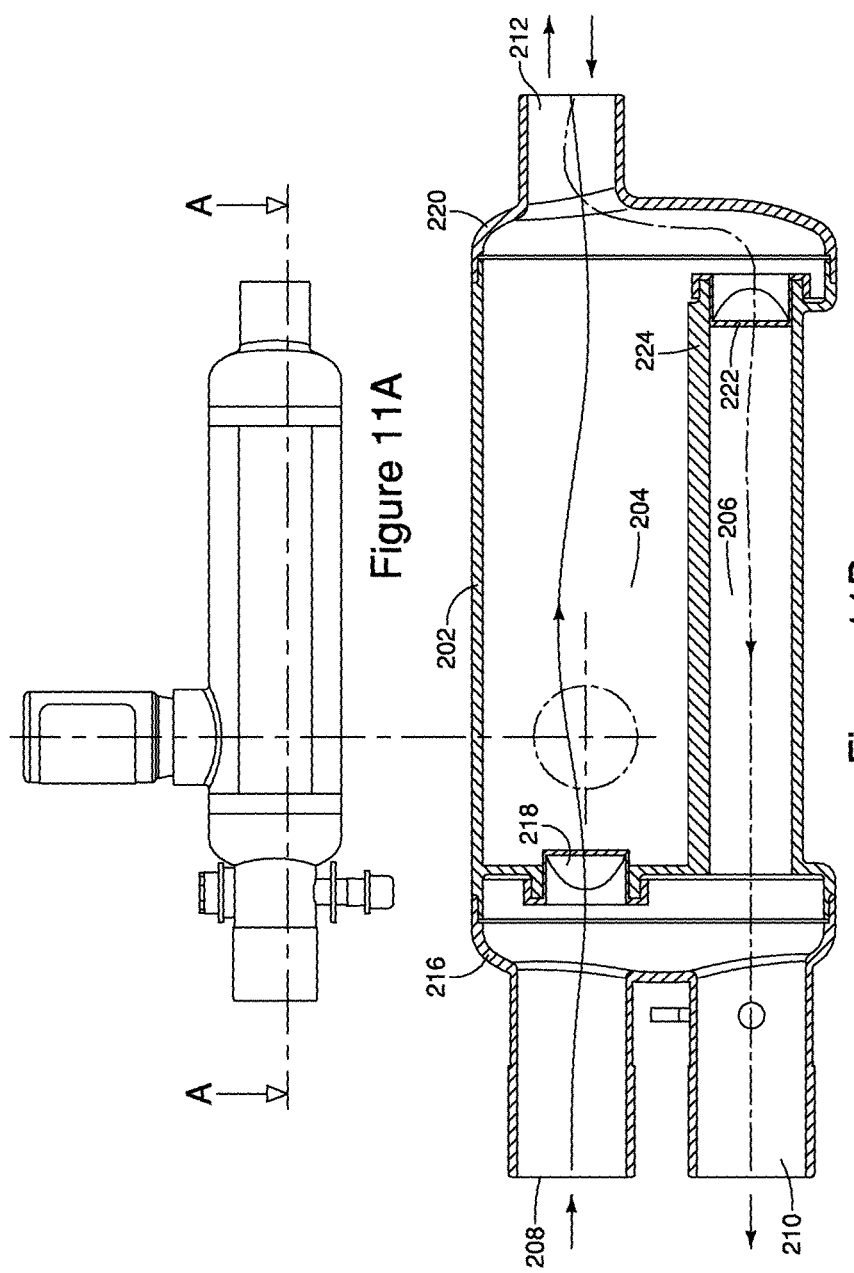

During operation, gases for inhalation and exhalation flow through the MDI ventilator assembly 200. Referring to FIGS. 9b and 11B, during inhalation, gases flow from the inhalation limb into the inhalation interior space 204 via the inhalation port 208 and the one-way inhalation valve 218, and flow from the inhalation interior space 204 to the endotracheal breathing tube, or tracheotomy tube, via the patient port 212. Likewise, referring to FIG. 26, gasses flow from the inhalation port 208 through the interior space 204 and through the one-way inhalation valve 218, to the patient port 212. In either embodiment, during inhalation, the one-way exhalation valve 222 blocks the flow of gasses from the exhalation interior space 206 to the endotracheal breathing tube, or tracheotomy tube, via the patient port 212.

As described above, when an MDI container 225 is inserted into the MDI receptacle 214, the actuator nozzle 226 of the MDI receptacle 214 engages a stem 228 extending from the MDI container 225 and causes an aerosolized drug to be dispensed into the inhalation interior space 204. Therefore, it will be appreciated that during inhalation, when gases flow from the inhalation interior space 204 to the endotracheal breathing tube, or tracheotomy tube, the aerosolized drug expand and flows to the patient. Further, if any portion of the aerosolized drug is not inhaled during an initial breath, the remaining aerosolized drug is inhaled during subsequent breaths.

Figure 10A:
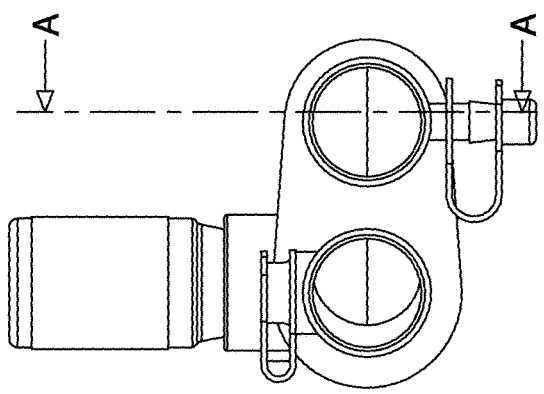
FIG. 10a is a front view of the MDI ventilator assembly of FIG. 7.
Figure 10B:
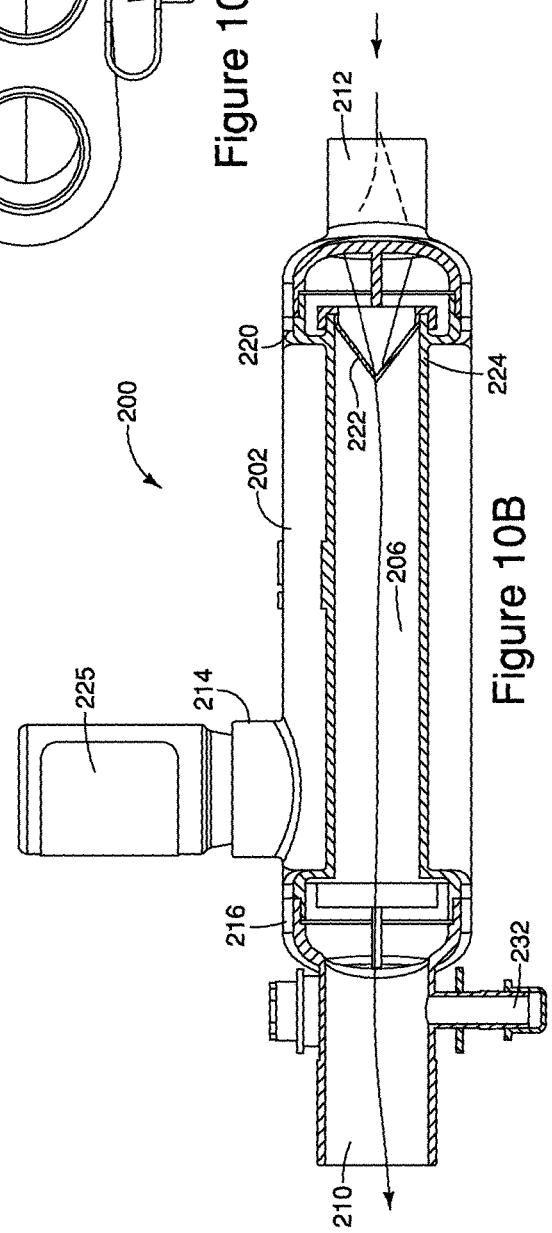
Figure 26:
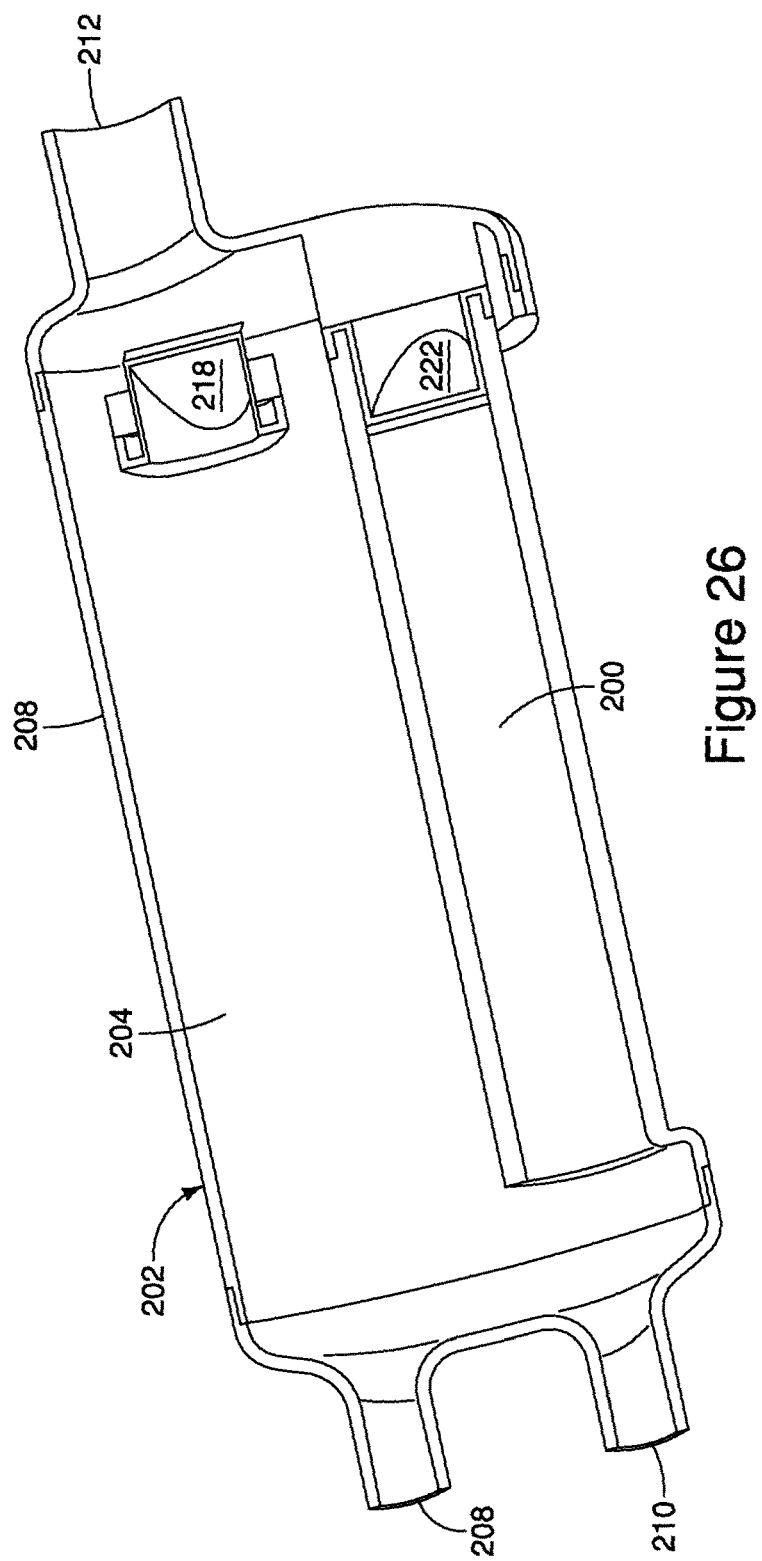
FIG. 26 is a cross-sectional view of another embodiment of an aerosol delivery system.
Figure 27:
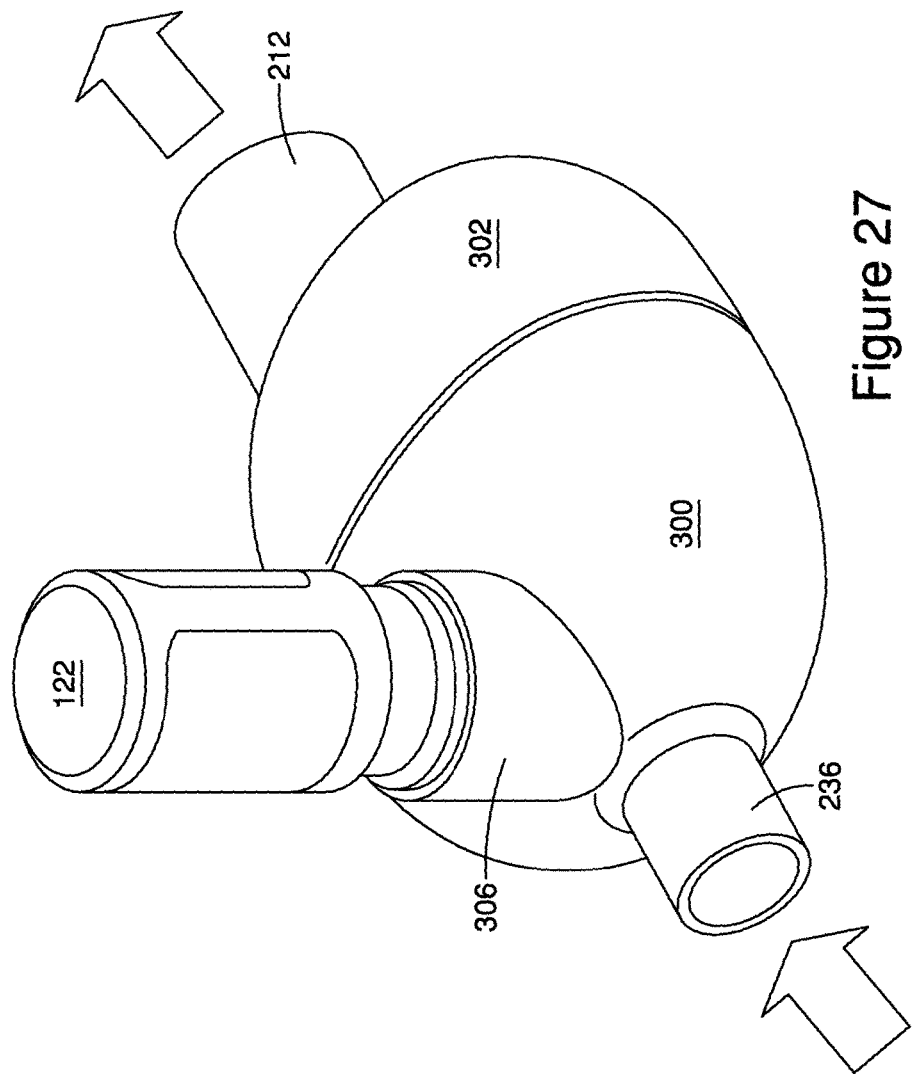
FIG. 27 is a perspective view of another embodiment of an aerosol delivery system.

Referring to FIGS. 10b, 11b and 26, during exhalation, gases, moisture, condensation, and/or mucus flow from the endotracheal breathing tube, or tracheotomy tube, to the exhalation interior space 206 via the patient port 212 and the one-way exhalation valve 222, and flow from the exhalation interior space 206 to the exhalation limb via the exhalation port 210. During exhalation, the one-way inhalation valve 218 blocks the flow of gases from the inhalation interior space 204 to the inhalation limb via the inhalation port 208. Because most of the gases, moisture, condensation, and/or mucus expelled by a patient flow out of into the exhalation interior space 206 and is blocked from being rebreathed by a patient due to the one-way exhalation valve 222 blocking flow from the exhalation interior space 206 to the patient port 212, the amount of gases, moisture, condensation, and/or mucus that are rebreathed by the patient is reduced.

Figure 7:
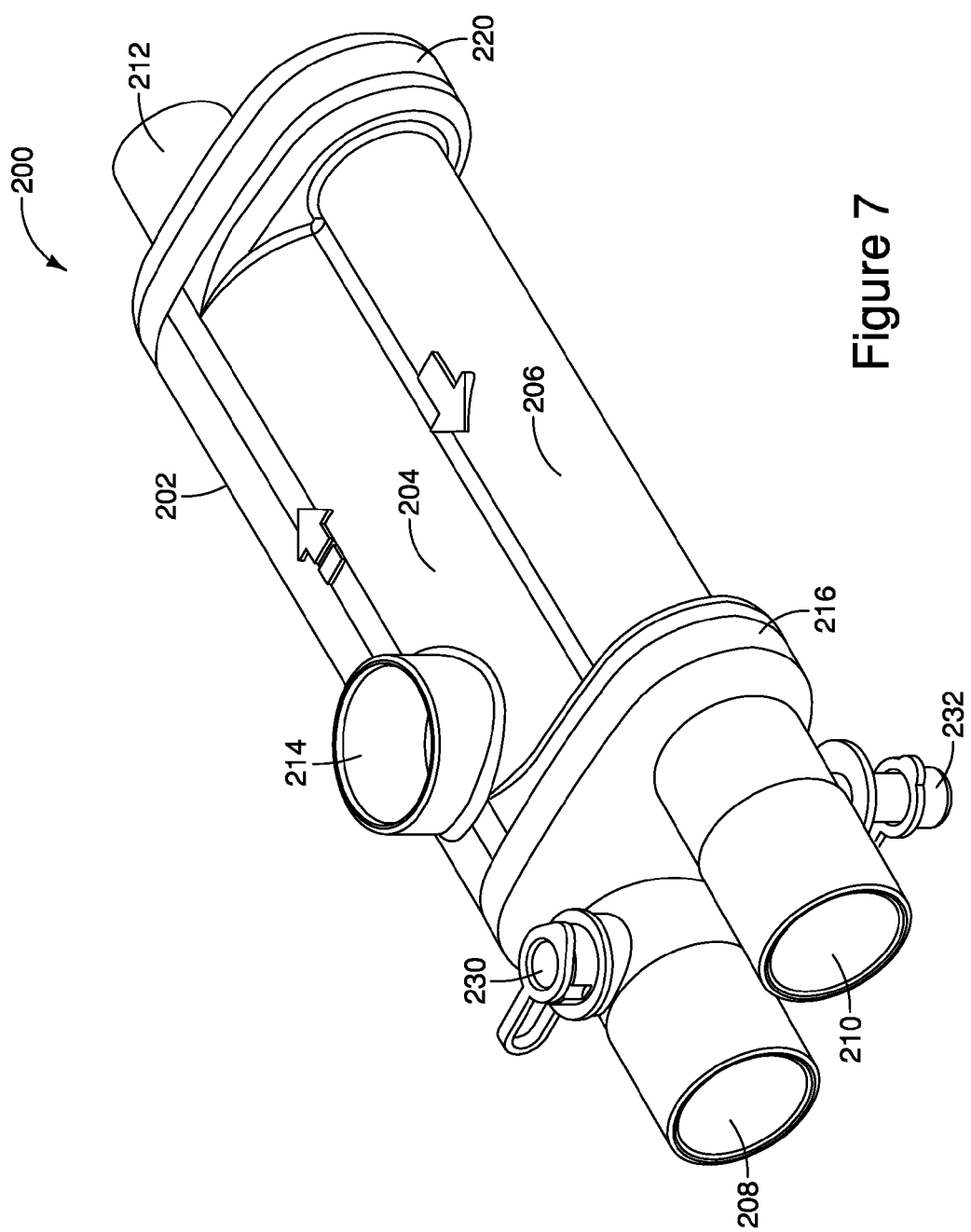
FIG. 7 is a perspective view of yet another embodiment of a MDI ventilator assembly.
Figure 8:
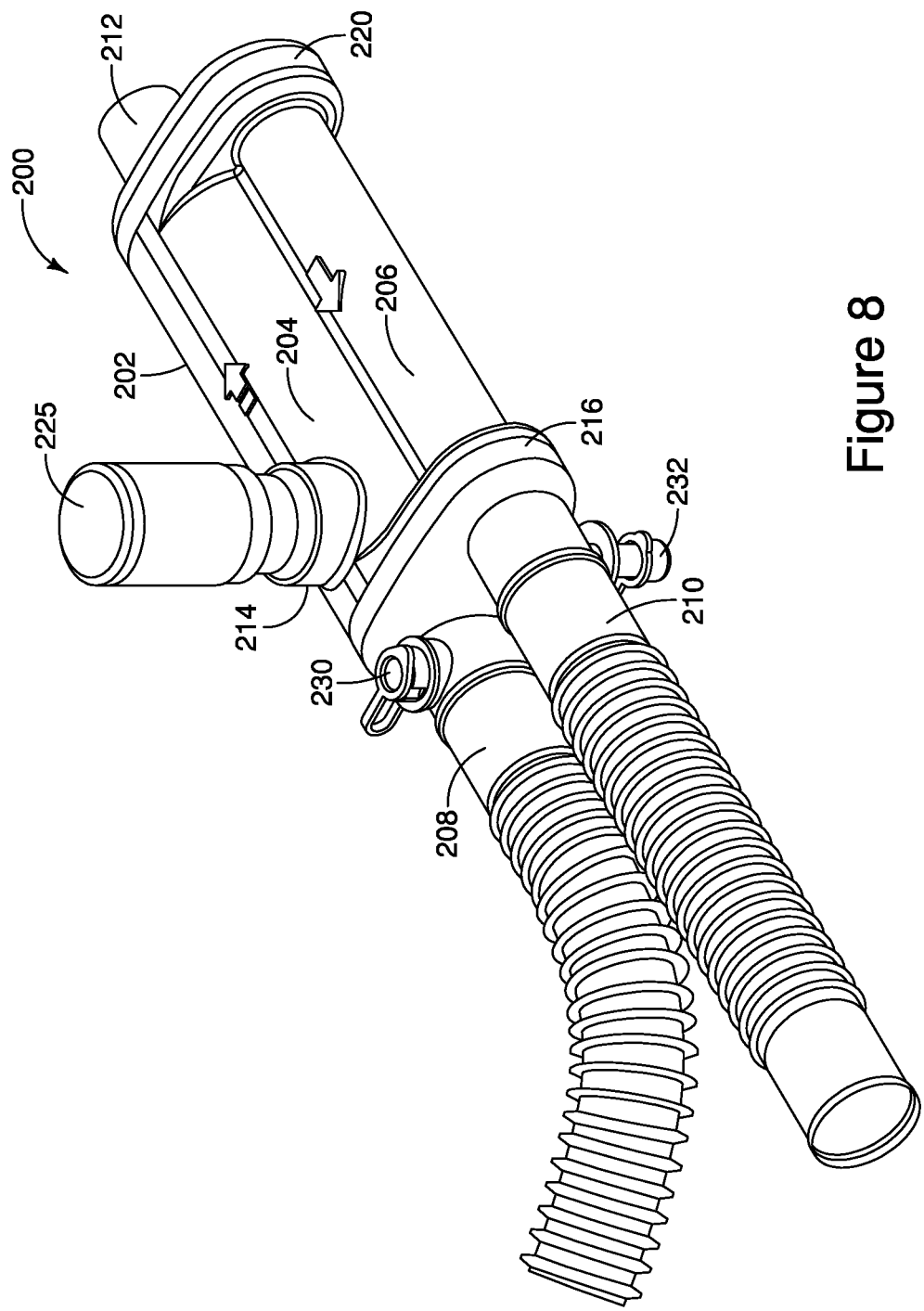
FIG. 8 is a perspective view of the MDI ventilator assembly of FIG. 7.
Figure 12:
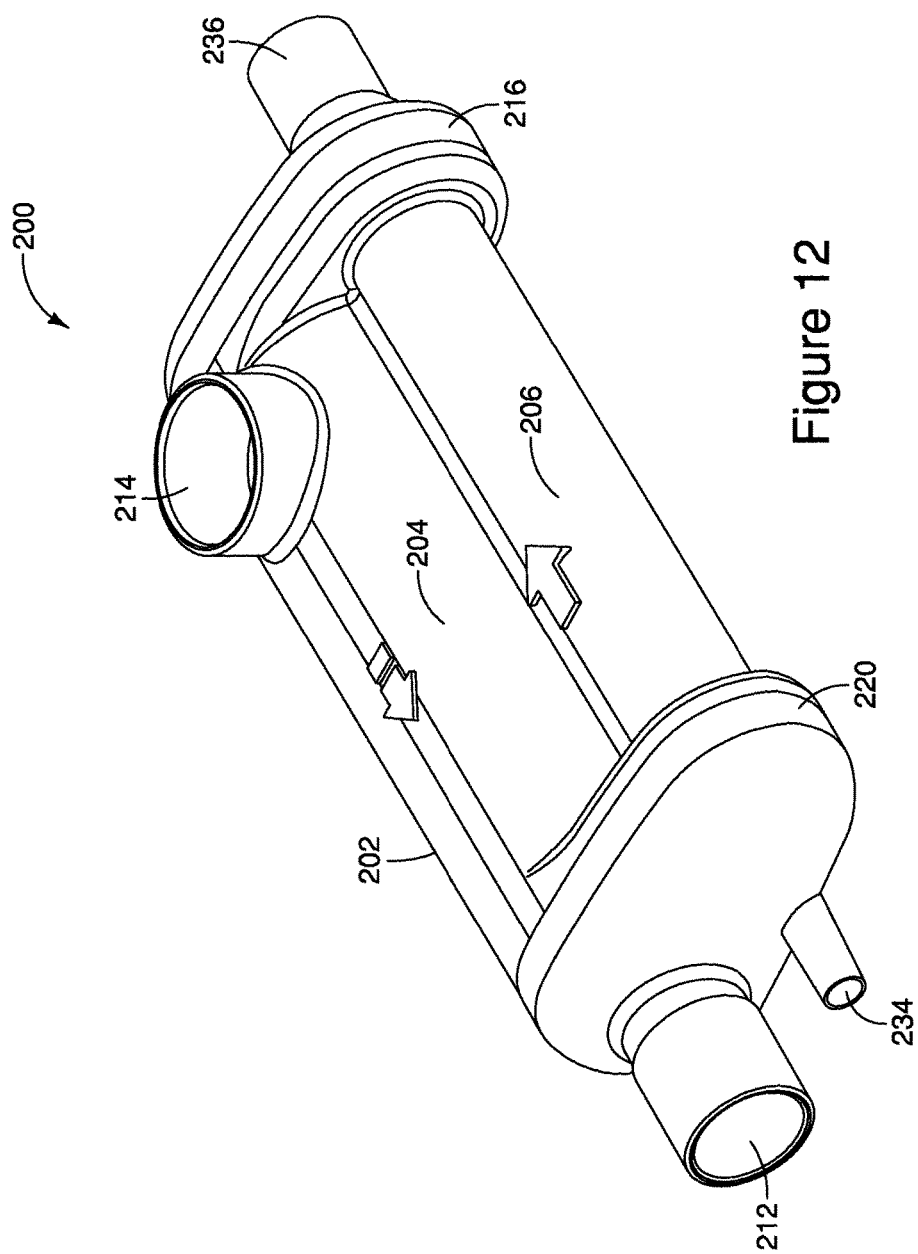
FIG. 12 is a perspective view of another embodiment of a MDI ventilator assembly.
Figure 14A:
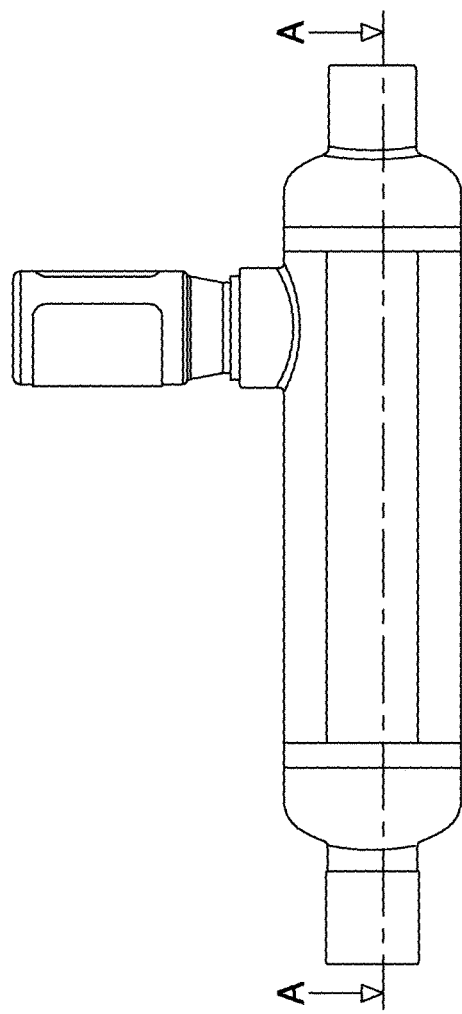
FIG. 14a is a side view of the MDI ventilator assembly of FIG. 12.
Figure 14B:
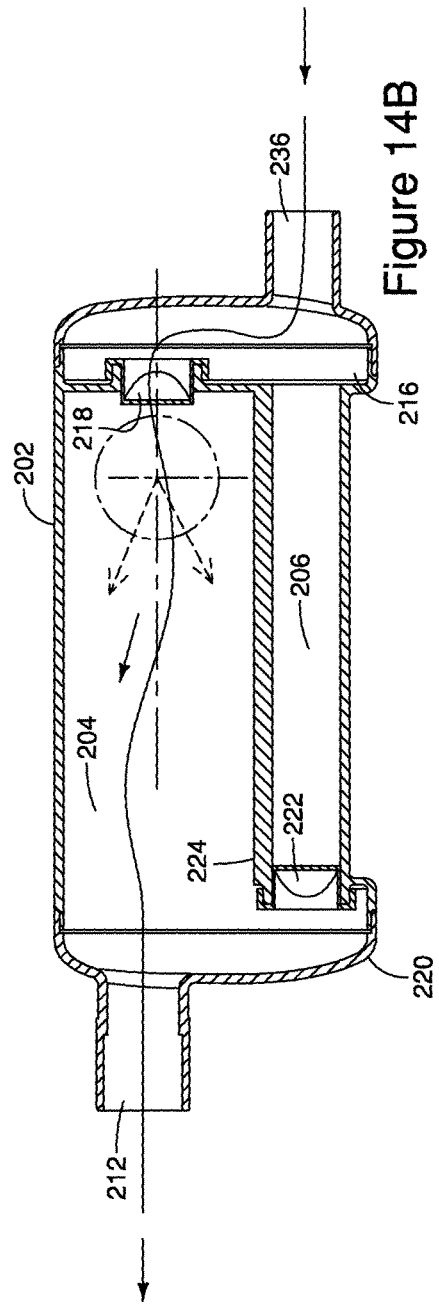
Figure 15A:
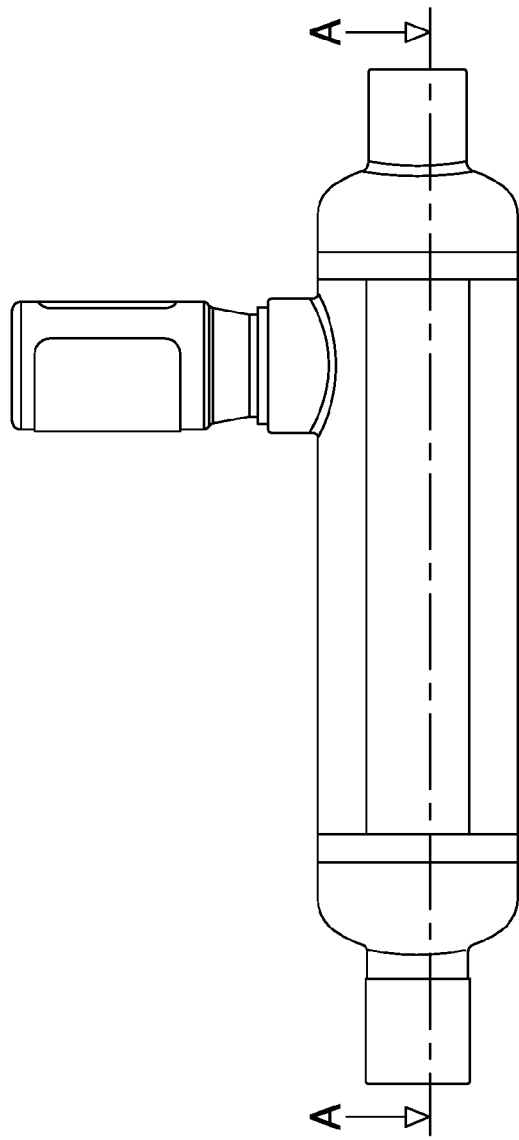
FIG. 15a is a side view of the MDI ventilator assembly of FIG. 12.
Figure 15B:
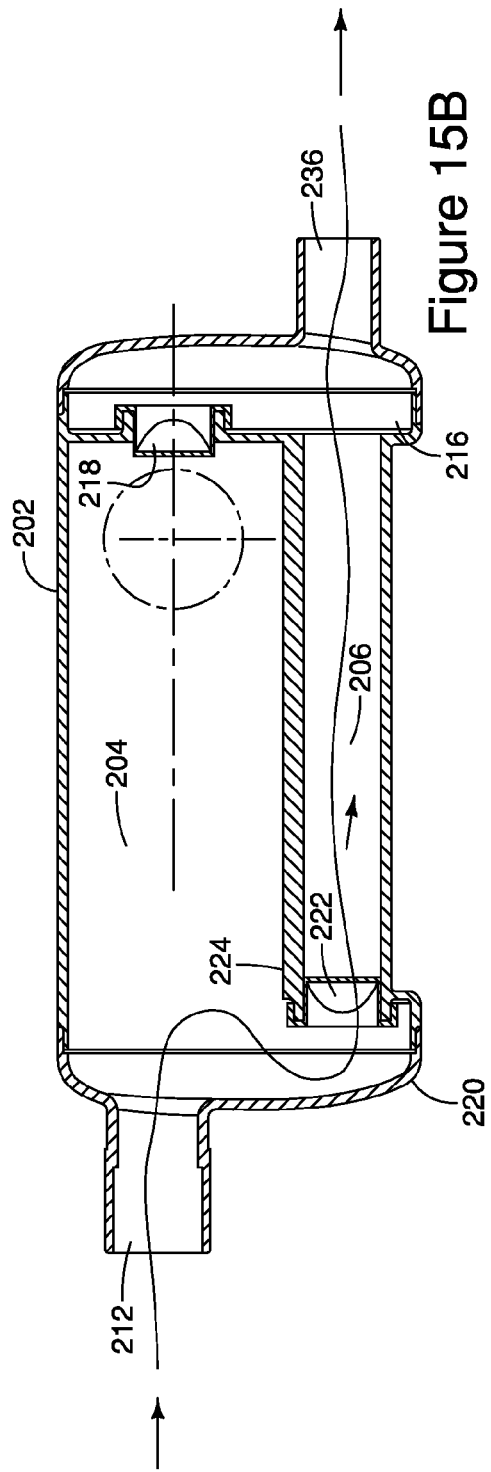
Figure 16:
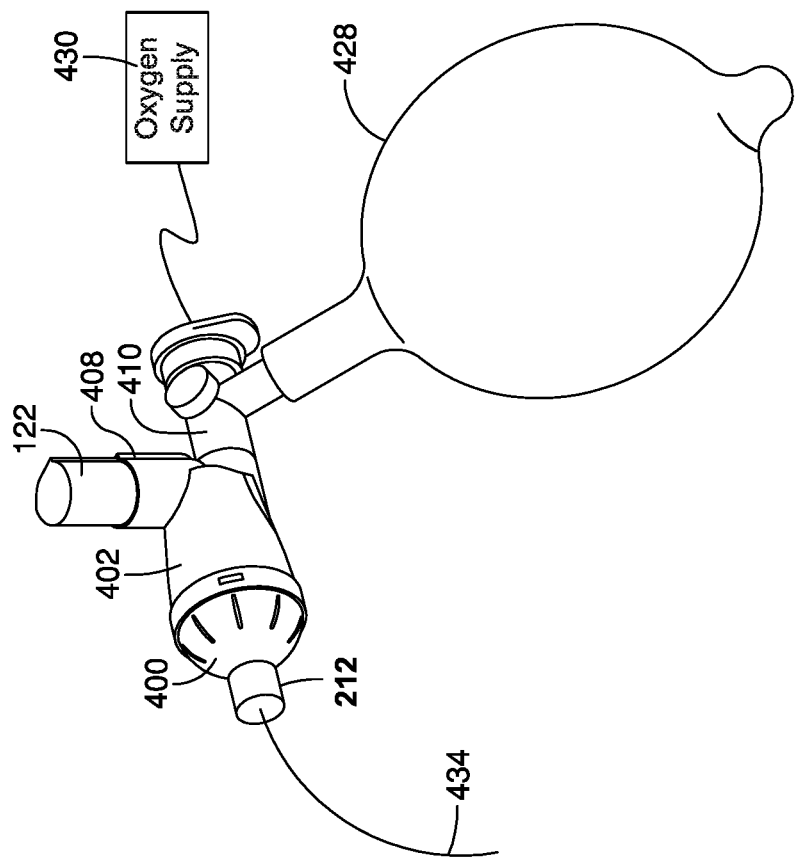
FIG. 16 is a perspective view of another embodiment of an aerosol delivery system configured with an endotracheal tube and a resuscitation bag.

As seen in FIGS. 7 and 12, the housing may additionally define a temperature probe port 230, a pressure monitoring port 232, and a moisture removal port 234. In one implementation, the temperature probe port 230 is positioned on the inhalation port 208 and the pressure monitoring port is positioned on the exhalation port 210. However, in other implementations, the temperature probe port 230 and/or pressure monitoring port 232 may be positioned at other locations on the housing 202.

Typically, the moisture removal port 234 is positioned on the same side of the housing 202 as the patient port 212, the second distal end 220 of the housing 202. However, the moisture removal port 234 may be positioned at other locations on the housing 202. The moisture removal port 234 provides for the removal of moisture, condensation, and/or mucus that may be expelled from the patient.

While the implementations described above with respect to FIGS. 7-11 have a distinct inhalation port 208 and exhalation port 210, as seen in FIGS. 12-25 and 27-35, in other implementations, the inhalation port and exhalation port may be combined into one ventilator port 236. The ventilator port 236 may be shaped in an annular manner with a radius such as 22 mm so that the ventilator port 208 may be inserted into a Wye connector in communication with an inhalation limb and an exhalation limb of a ventilator system. However, the ventilator port 236 may be other sizes and shapes. For example, the ventilator port 236 may be shapes such as a triangular port or a square port.

In this implementation with respect to the embodiment of FIGS. 12-15, during inhalation, gases flow from the inhalation limb through the Wye connector and into the inhalation interior space 204 via the ventilator port 236 and the one-way inhalation valve 218, which is located adjacent the ventilator port 236. The gases then flow through the inhalation interior space 204 to the endotracheal breathing tube, or tracheotomy tube, via the patient port 212. Alternatively, and referring to the embodiments of FIGS. 27-35, the gases flow from the ventilator port 236 into the interior space 204 and then through the one-way valve 218, which is located adjacent the patient port 212. In either embodiment, as described above, when an MDI container 225 is placed in the MDI receptacle 214, an aerosolized drug is dispensed into the inhalation interior space 204. Therefore, it will be appreciated that during inhalation, when gases flow from the inhalation interior space 204 to the patient, the aerosolized drug also flows to the patient.

During exhalation, and referring to the embodiment of FIGS. 12-25 and 27-35, gases flow from the endotracheal breathing tube, or tracheotomy tube, to the exhalation interior space 206 via the patient port 212 and the one-way exhalation valve 222, and from the exhalation interior space 206 to the exhalation limb via the ventilator port 236.

Figure 28:
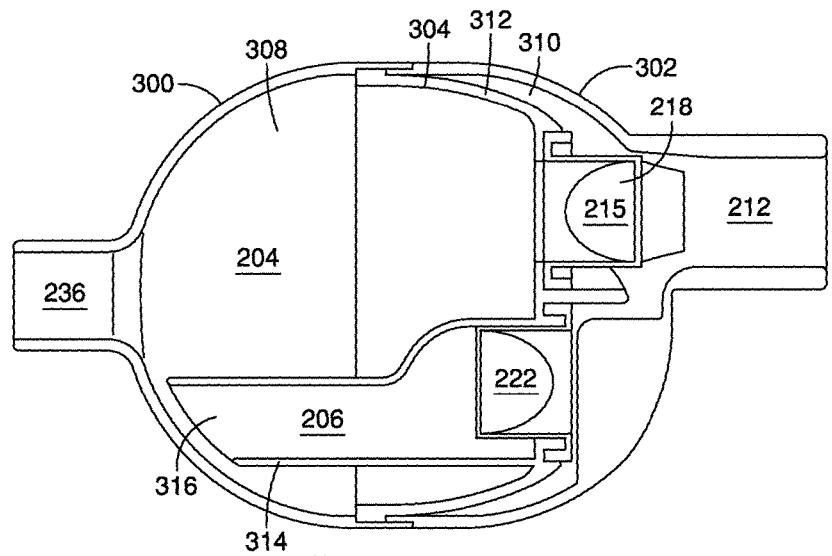
FIG. 28 is a cross-sectional view of the aerosol delivery system shown in FIG. 27.
Figure 29:
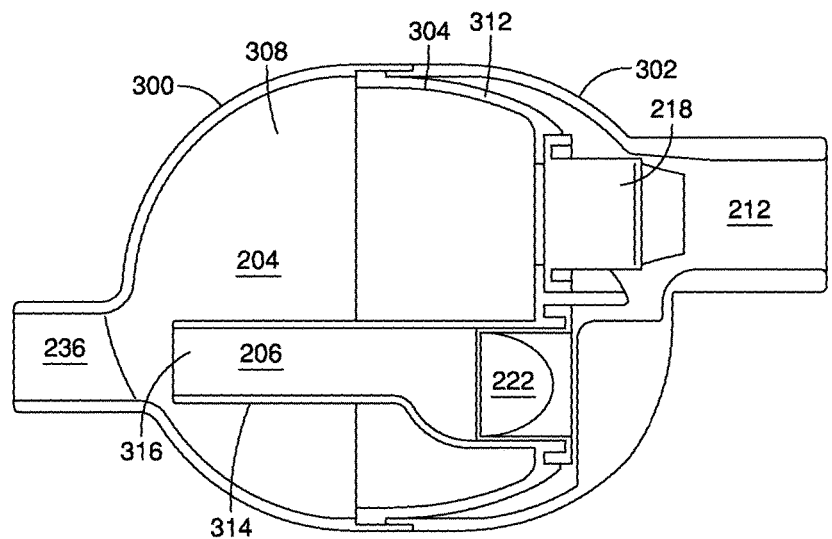
FIG. 29 is a cross-sectional view of an alternative embodiment of an aerosol delivery system.
Figure 30:
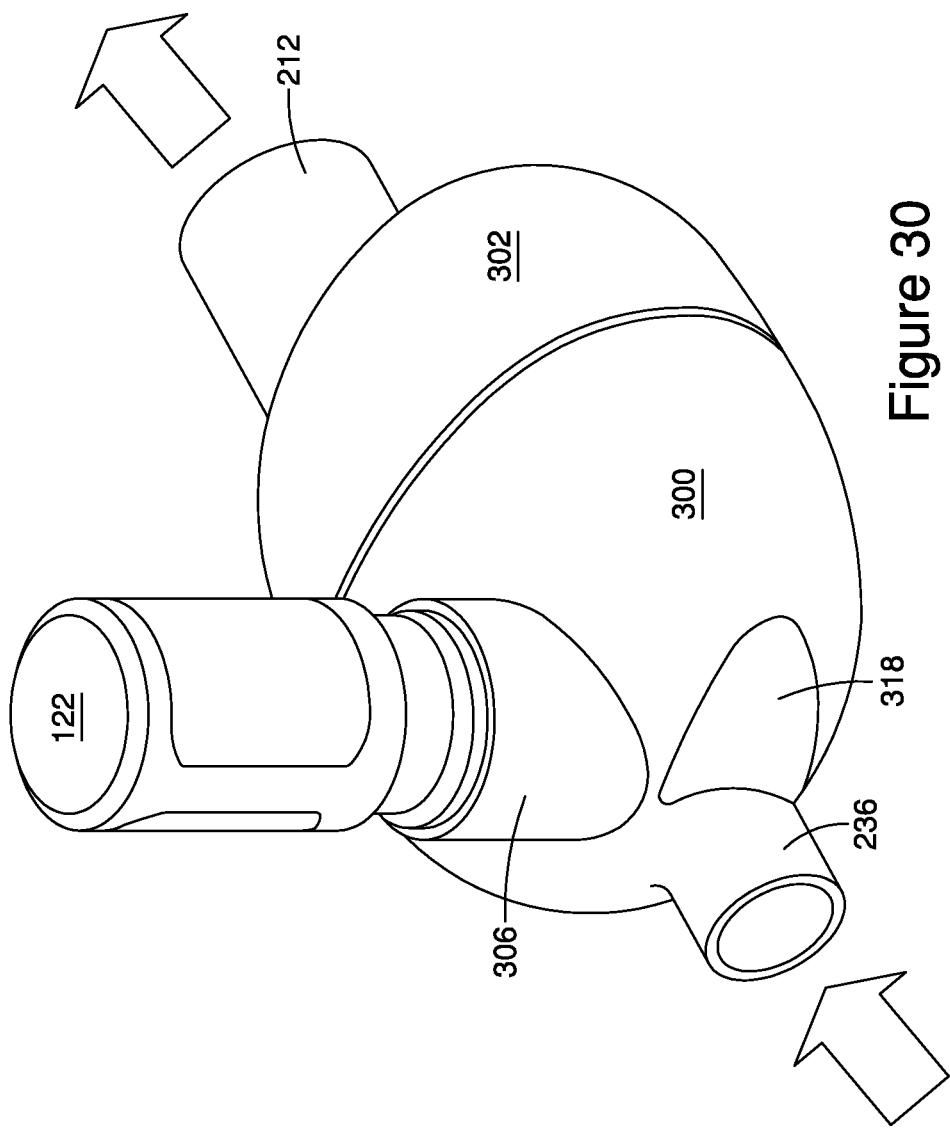
FIG. 30 is a perspective view of another embodiment of an aerosol delivery system.
Figure 31:
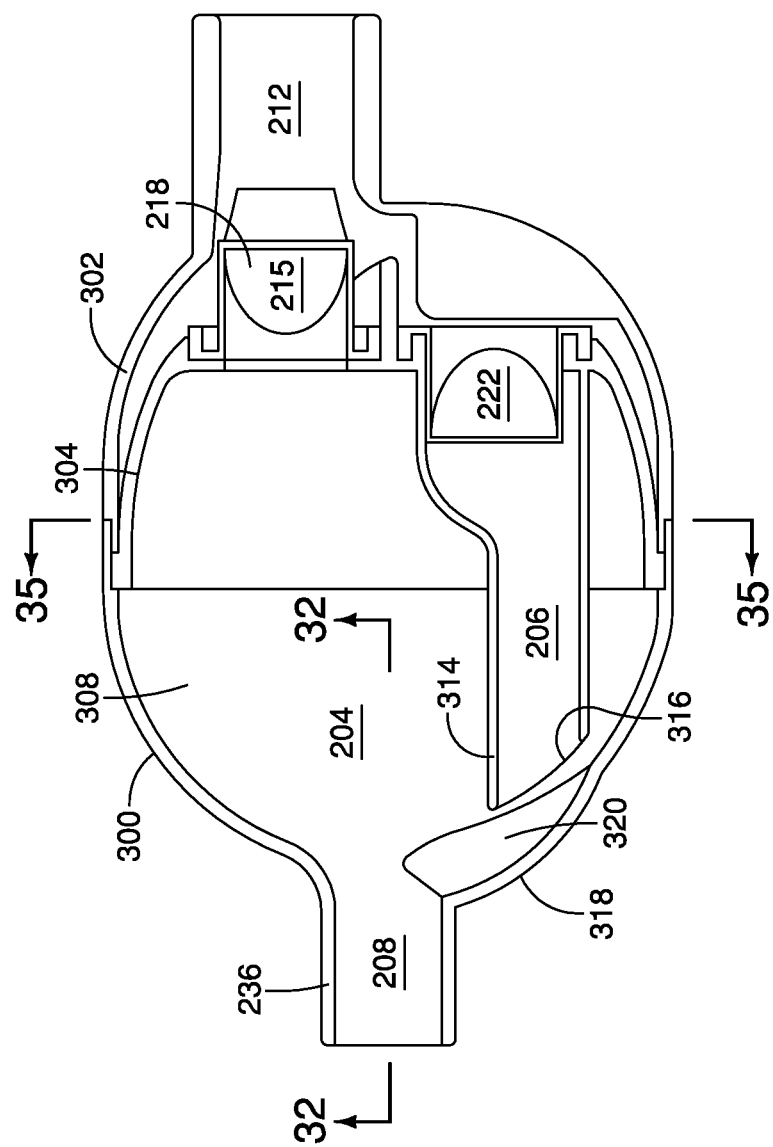
FIG. 31 is a cross-sectional view of the aerosol delivery system shown in FIG. 30.
Figure 32:
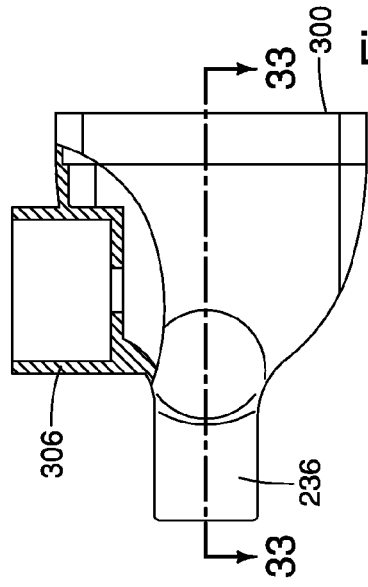
FIG. 32 is a cross-sectional view of the aerosol delivery system taken along line 32-32 of FIG. 31.
Figure 33:
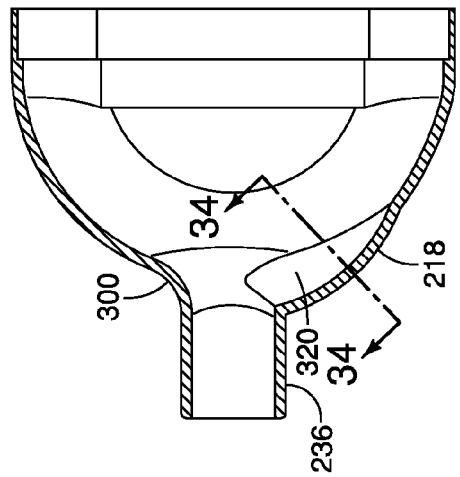
FIG. 33 is a cross-sectional view of the aerosol delivery system taken along line 33-33 of FIG. 32.
Figure 34:
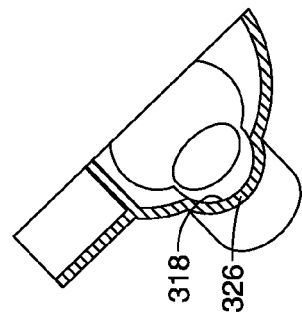
FIG. 34 is a cross-sectional view of the aerosol delivery system taken along line 34-34 of FIG. 33.
Figure 35:
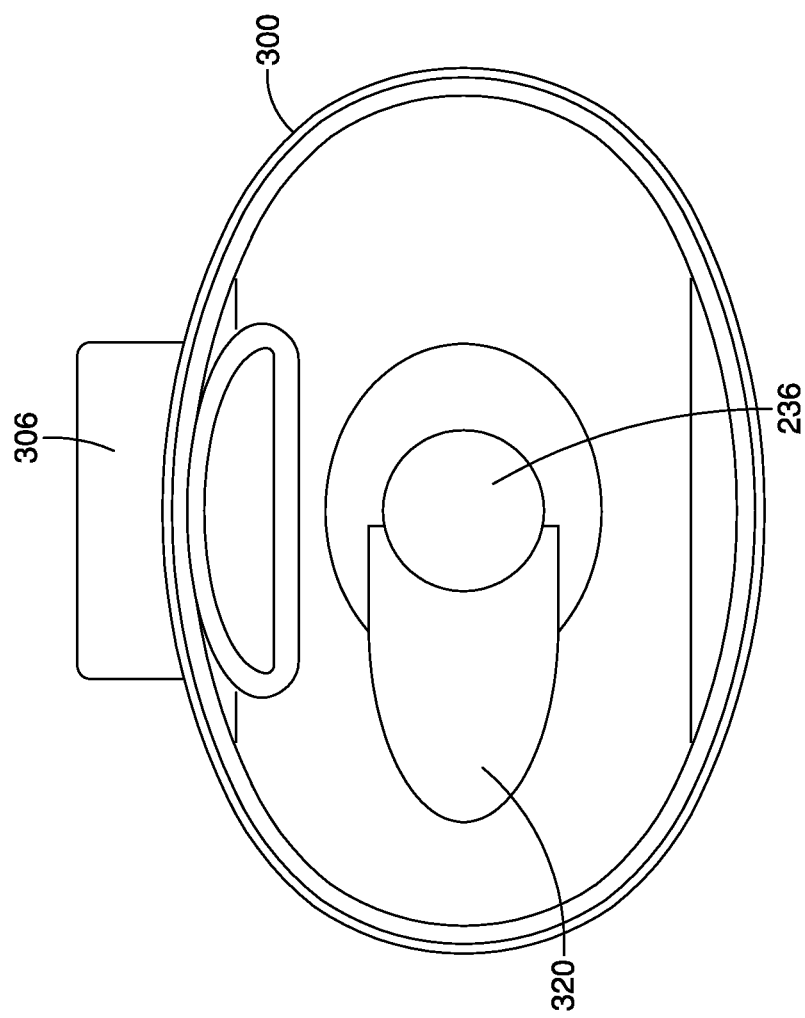
FIG. 35 is a cross-sectional view of the aerosol delivery system taken along line 35-35 of FIG. 31.

Referring to the embodiments of FIGS. 27-35, the housing is formed from three components 300, 302, 304 that are snap-fit, or otherwise connected. The first housing component 300 includes the ventilator port 236, a receptacle 306 having a well 350 with an orifice 352 that communicates with a generally open chamber 308 defining in part the inhalation interior space 204. The second housing component 302 includes the patient port 212 and a generally open chamber 310. The third component 304 includes a chamber portion 312 defining a portion of the inhalation interior space 204 in combination with the interior space of the first housing component 300, and a tube 314 disposed in and extending upstream towards the ventilator port 236, with the tube 314 defining the exhalation interior space 206. The third component 304 is secured between the first and second housing components 300, 302 and includes the inhalation and exhalation valves 218, 222. When assembled, the exhalation tube 314 has an outlet 316 that can be aligned with the ventilator port as shown in FIG. 29, or offset therefrom. The outlet 316 can be tapered or otherwise shaped to fit or conform to the first component 300 as shown in FIG. 28, or the first housing component can include an additional bump 318 defining an interior pocket 320, which channels the gases from the outlet to the ventilator port while permitting the outlet to be offset from the ventilator port.

Now referring to the embodiment of FIGS. 16-25, the housing again includes three primary components as shown in FIG. 18, for example. The first housing component 400 includes the patient port 212. It should be understood that the first housing components 300, 400 can be configured with different patient ports to accommodate various patient interface components, including for example and without limitation ET tubes, masks, mouthpieces, etc. The second housing component 402 includes an exterior wall 404 and an interior wall 406, or shelf, which separates the chamber into the inhalation and exhalation interior spaces 204, 206. In one embodiment, the spaces 204, 206 communicate with each other at a vestibule area formed in front of and communicating with the patient port. A receptacle 408 is formed on the housing and includes a well having an orifice that communicates directly with the inhalation interior space 204.

The third housing component 410 is formed as a connector and defines the ventilator port 236. The connector has first and second passageways 412, 414 separated by a wall. Additional walls 416 form a valve seat for the inhalation valve 418. The first and third components 400, 410 are secured to respective ends of the second component 402 to form the housing. An integrally formed inhalation/exhalation valve 418, 420 is disposed between the connector 410 and the second component 402. The second component 402 has a valve seat 422 for the exhalation valve. The valve includes a base portion 424, and inhalation/exhalation flaps 418, 420 extending in opposite directions from the base portion 422. The inhalation valve 418 moves off of the first seat 416 of the connector during inhalation, while the exhalation valve 420 moves off of the second seat 422 during exhalation. In one embodiment, the surface area of the inhalation valve 418 is greater than the surface area of the exhalation valve 420, although it should be understood that the surface areas can be the same, or that the surface area of the inhalation valve is less than the area of the exhalation valve. It should be understood that the inhalation and exhalation valves 418, 420 can be formed separately, again with the same or differential surface areas.

Figure 17A:
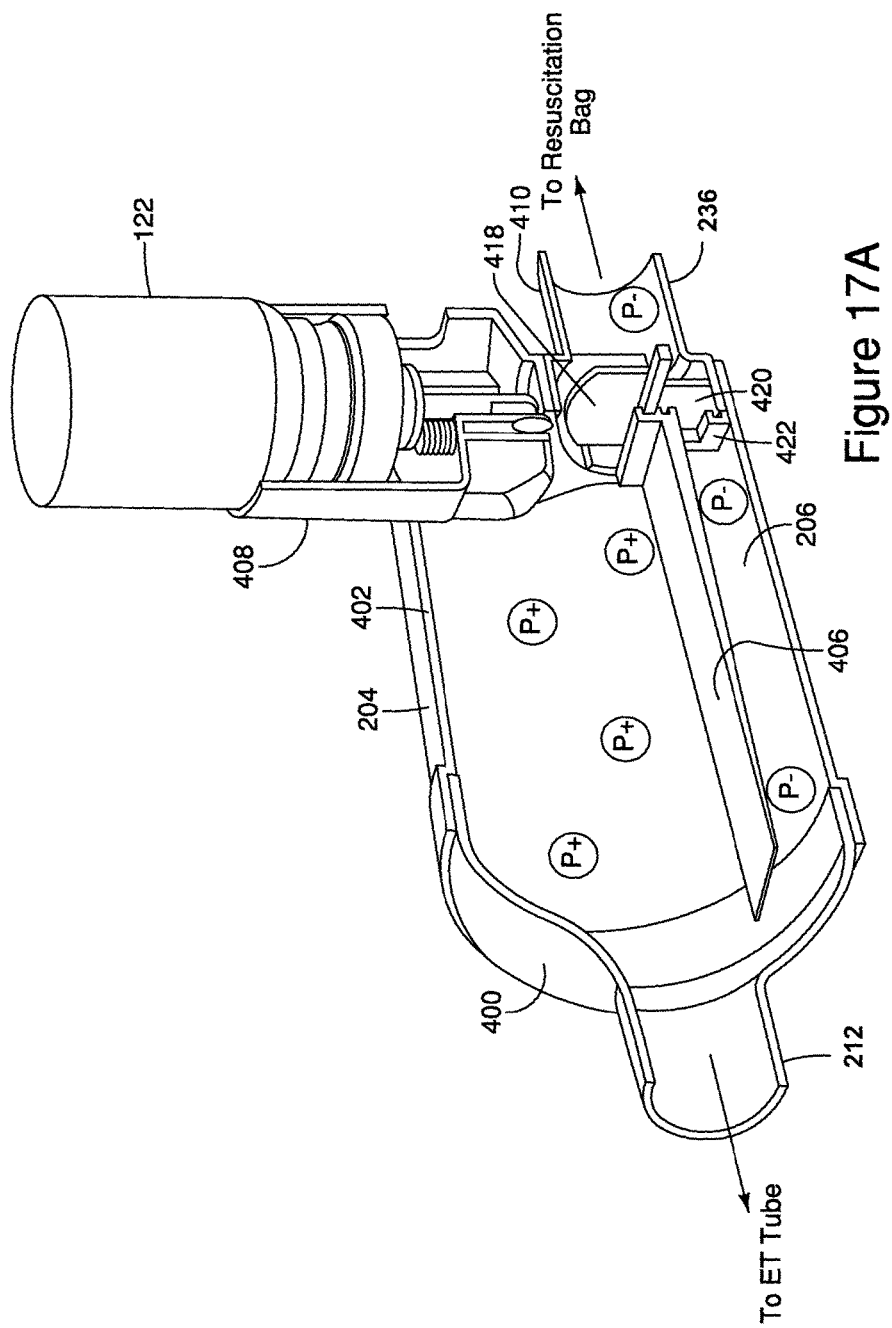
FIGS. 17A-D are cut-away views of the embodiment shown in FIG. 16 without the endotracheal tube or resuscitation bag in different phases of a breathing cycle.
Figure 17B:
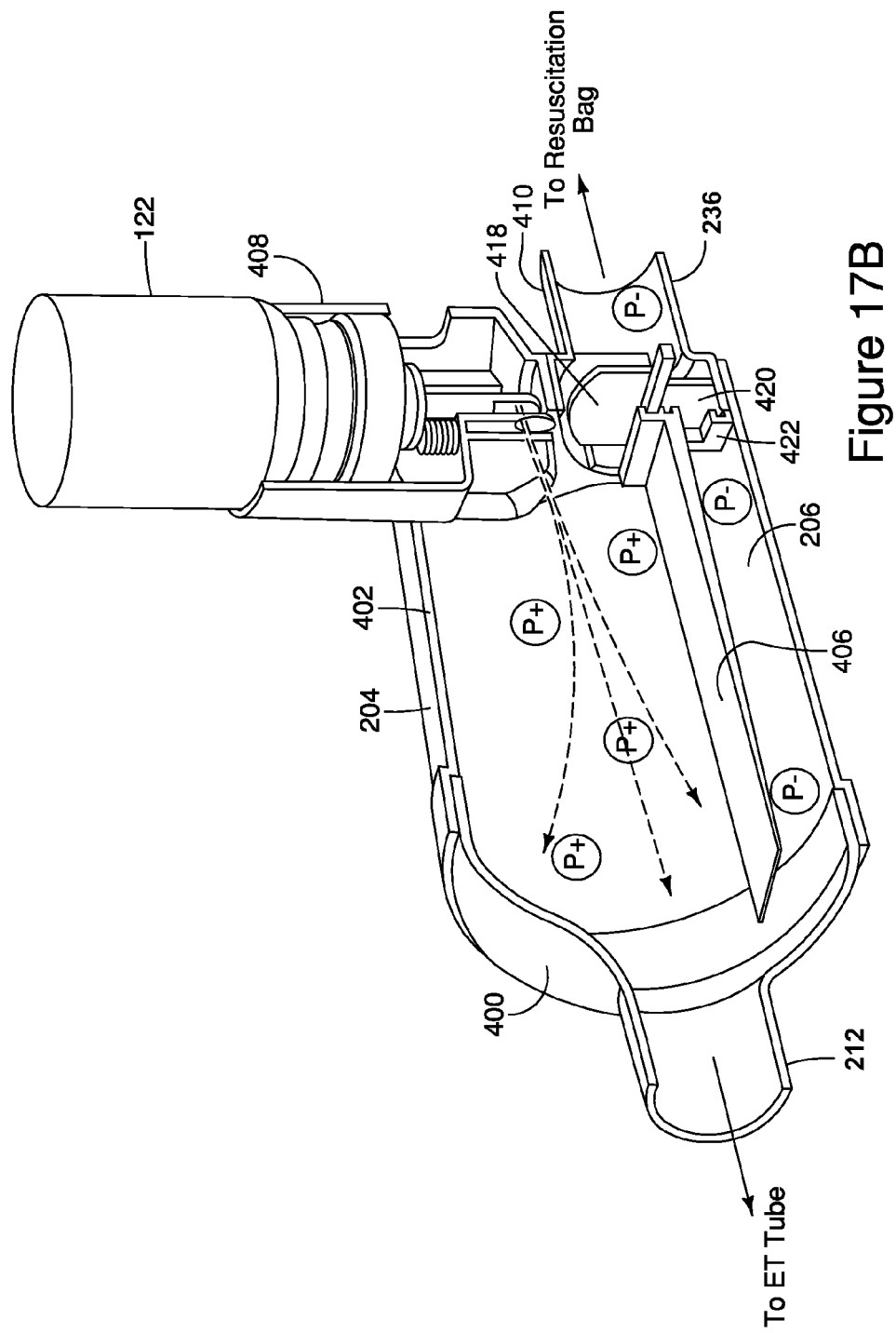
Figure 17C:
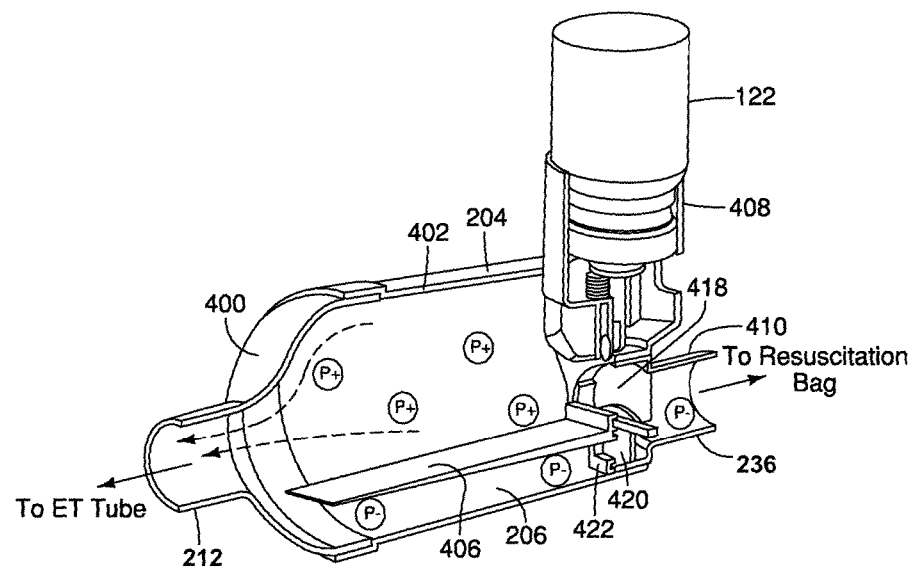
Figure 17D:
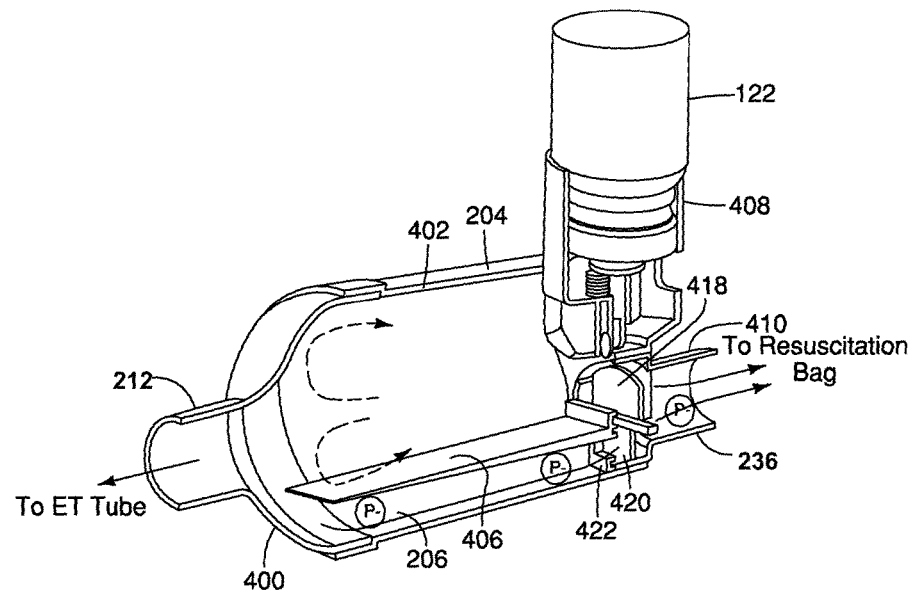
Figure 18:
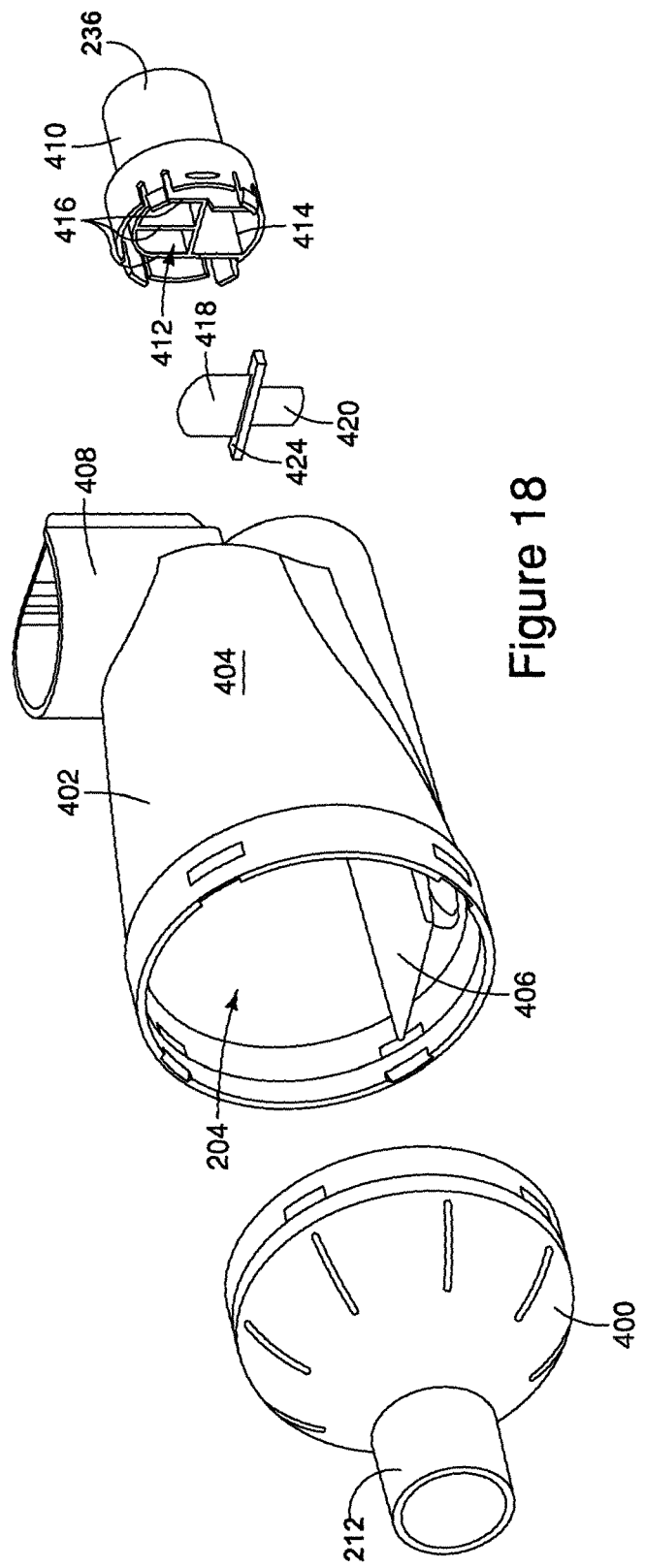
FIG. 18 is an exploded, perspective view of the aerosol delivery system shown in FIG. 16 without the endotracheal tube or resuscitation bag.
Figure 20:
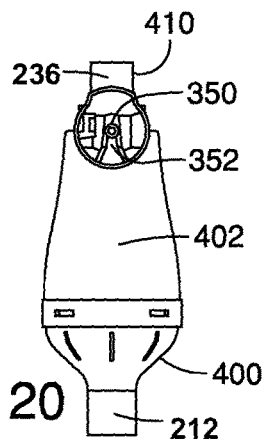
FIG. 20 is a top view of the aerosol delivery system shown in FIG. 19.
Figure 19:
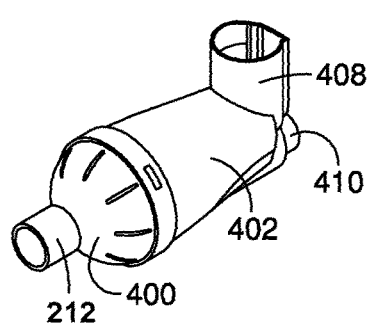
FIG. 19 is a perspective view of the aerosol delivery system shown in FIG. 16 without the endotracheal tube or resuscitation bag.
Figure 22:
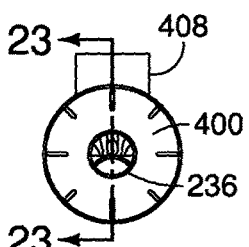
FIG. 22 is a patient-side end view of the aerosol delivery system shown in FIG. 19.
Figure 21:
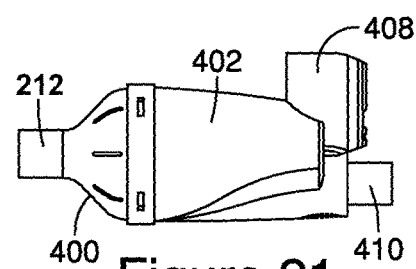
FIG. 21 is a side view of the aerosol delivery system shown in FIG. 19.
Figure 23:
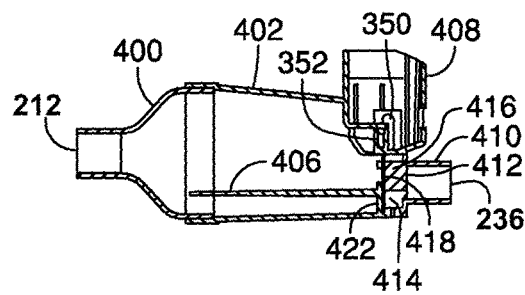
FIG. 23 is a cross-sectional view of the aerosol delivery system taken along line 23-23 of FIG. 22.
Figure 24:
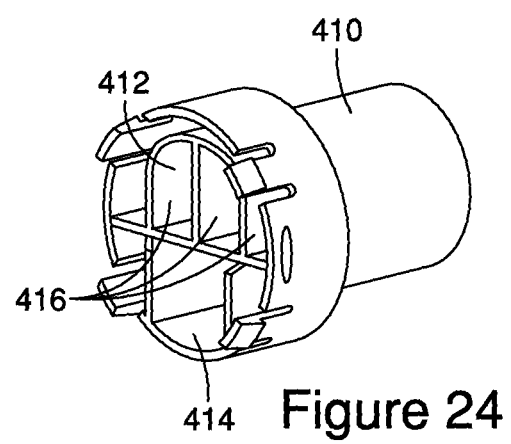
FIG. 24 is a perspective view of a connector component.
Figure 25:
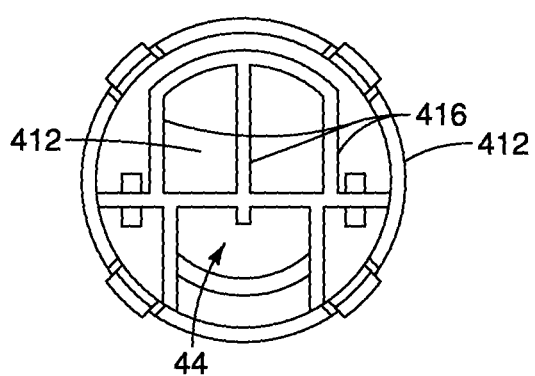
FIG. 25 is an end view of the connector component shown in FIG. 24.

In operation, as shown in FIGS. 16 and 17A-D, the system is pressurized to inflate the lungs of the patient, such as neonate. The positive pressure comes from an oxygen supply 430 connected to a resuscitation bag 428. Manual resuscitation, for example and without limitation bagging, begins immediately to maintain the neonate's breathing. The pressurized metered dose inhaler (pMDI) 122 is actuated or fired in between breaths as shown in FIG. 17B, with the drug being held in the inhalation interior space 204 of the chamber until the next breath. As shown in FIG. 17C, as the resuscitation bag is squeezed, the flow through the inhalation valve 418 and increase in pressure forces the drug from the inhalation interior space 204 of the chamber through the patient port 212 to the patient, for example through the endotracheal tube 434. As shown in FIG. 17d, as the resuscitation bag 428 reinflates, it creates a negative pressure that pulls air through the exhalation interior space 206 as the exhalation valve 420 is opened, with any drug remaining in the inhalation interior space 204 staying there due to the separation of the inhalation and exhalation interior spaces 204, 206. The next breath forces the remaining drug through the patient port 212 to the patient through the patient interface component.

While the embodiments of FIGS. 12-25 and 27-35 may still be used with a Wye connector, it should be understood that because inspired gas flow and expired gas flow are separated at the entrance to the endotracheal breathing tube, or tracheotomy tube, the MDI ventilator assembly may be moved from the inspired limb and connected directly to the endotracheal breathing tube or tracheotomy tube.

FIGS. 1-35 disclose ventilator circuit aerosol delivery systems for use with intermittent flow ventilators and continuous flow ventilators, and including without limitation both mechanical and manual ventilators such as resuscitation bags. As used herein throughout, the term "including" does not means limited to, but rather is without limitation. Implementations of the disclosed ventilator circuit aerosol delivery systems provide the ability to connect the MDI ventilator assembly directly to the endotracheal tube, or a tracheotomy tube, due to an integrated Wye connector or the ability to separate inhalation flow and exhalation flow at the entrance to an endotracheal breathing tube or a tracheotomy tube. Connecting the MDI ventilator assemblies directly to the endotracheal tube, or tracheotomy tube, provides the ability to more efficiently administer aerosolized drugs to a patient without "dead space area" where gases exhaled from a patient remain between each breath such that the same gases are inhaled by the patient upon their next breath. For this reason, the MDI ventilator assembly may be safely left in a ventilator circuit even when the MDI ventilator assembly is not being used to administer an aerosolized drug to a patient so that it is no longer necessary to break a ventilator circuit each time an aerosolized drug is administered to a patient.

It is therefore intended that the foregoing detailed description be regarded as illustrative rather than limiting, and that it be understood that it is the following claims, including all equivalents, that are intended to define the spirit and scope of this invention.

The invention claimed is:

1. A ventilator assembly for use in a ventilator circuit for administering medication to a patient, the ventilator assembly comprising:
   a housing defining an interior space;
   an inhalation port, the inhalation port defining an inhalation passageway in communication with the interior space;
   an exhalation port, the exhalation port defining an exhalation passageway in communication with the interior space, wherein the inhalation and exhalation ports communicate with a single ventilator port positioned at a first location on the housing, wherein the inhalation and exhalation ports are not in direct fluid communication with an ambient environment surrounding the housing;
   a patient port positioned at a second location on the housing, wherein the first and second locations are spaced apart on the housing such that the patient port is separate and spaced from the ventilator port, the patient port defining a patient passageway in communication with the interior space; and
   a receptacle positioned on the housing and in communication with the interior space, the receptacle operative to receive a container comprising an aerosolized medication.

2. The ventilator assembly of claim 1 further comprising a one-way inhalation valve positioned in the housing to permit one-way flow from the inhalation port to the patient port, and a one-way exhalation valve positioned in the housing to permit one-way flow from the patient port to the exhalation port.

3. The ventilator assembly of claim 1, wherein the receptacle is a metered dose inhaler ("MDI") receptacle and the container is a MDI container.

4. The ventilator assembly of claim 1, wherein the inhalation port is in communication with the interior space at a first end of the housing and the exhalation port is in communication with the interior space at a second end of the housing that opposes the first end of the housing.

5. The ventilator assembly of claim 1, wherein the exhalation port is in communication with the interior space at a bottom of the housing.

6. The ventilator assembly of claim 5 wherein the inhalation port defines a first axis and the exhalation port defines a second axis, wherein the first and second axes are non-parallel and form an acute angle therebetween.

7. The ventilator assembly of claim 5 wherein the inhalation port defines a first axis and the exhalation port defines a second axis, wherein the first and second axes are parallel.

8. The ventilator assembly of claim 1, wherein the receptacle is positioned on a top of the housing.

9. The ventilator assembly of claim 1, further comprising:
   a temperature probe port positioned on the housing and in communication with the interior space.

10. The ventilator assembly of claim 1, further comprising:

a pressure port positioned on the housing and in communication with the interior space.

11. The ventilator assembly of claim 1 further comprising a one-way inhalation valve positioned in the housing to permit one-way flow from the inhalation port to the patient port.

12. The ventilator assembly of claim 11 further comprising a one-way exhalation valve positioned in the housing to permit one-way flow from the patient port to the exhalation port.

13. The ventilator assembly of claim 1 wherein the exhalation port has an outlet that opens into and is in direct fluid communication with the interior space.

14. The ventilator assembly of claim 1 wherein the exhalation port has an inlet that opens into and is in direct fluid communication with the interior space.

15. The ventilator assembly of claim 11 wherein the inhalation valve is located adjacent the patient port.

16. The ventilator assembly of claim 11 wherein the inhalation valve is located adjacent the ventilator port.

17. The ventilator assembly of claim 12 wherein the exhalation valve is located adjacent the patient port.

18. The ventilator assembly of claim 12 wherein the exhalation valve is located adjacent the ventilator port.

* * * * *